United States Patent
Shohmi et al.

(10) Patent No.: US 10,161,951 B2
(45) Date of Patent: Dec. 25, 2018

(54) SPECIMEN PROCESSING APPARATUS FOR GENETIC TESTING

(71) Applicant: Sysmex Corporation, Kobe-shi, Hyogo (JP)

(72) Inventors: Keiichiro Shohmi, Kobe (JP); Ryousuke Ishitsubo, Kobe (JP); Shoichiro Asada, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 8 days.

(21) Appl. No.: 15/190,714

(22) Filed: Jun. 23, 2016

(65) Prior Publication Data
US 2017/0003310 A1    Jan. 5, 2017

(30) Foreign Application Priority Data

Jun. 30, 2015   (JP) .................................. 2015-132131

(51) Int. Cl.
*G01N 35/10*    (2006.01)
*B01L 3/02*    (2006.01)
(Continued)

(52) U.S. Cl.
CPC ........ G01N 35/1011 (2013.01); B01L 3/0237 (2013.01); B01L 3/0279 (2013.01); B01L 3/5085 (2013.01); C12Q 1/68 (2013.01); G01N 35/00584 (2013.01); G01N 35/1002 (2013.01); G01N 35/1065 (2013.01); G01N 35/1081 (2013.01); B01L 7/52 (2013.01); B01L 9/523 (2013.01); B01L 2200/16 (2013.01);
(Continued)

(58) Field of Classification Search
CPC .................................................. G01N 35/1011
USPC ........................................................ 435/286.5
See application file for complete search history.

(56) References Cited

U.S. PATENT DOCUMENTS

2003/0012699 A1* 1/2003 Moore ............... G01N 35/0098
422/400
2004/0096365 A1   5/2004 Toi et al.
(Continued)

FOREIGN PATENT DOCUMENTS

EP           2 848 698 A1    3/2015
WO    WO 2010/118016 A2    10/2010

OTHER PUBLICATIONS

Lee et al., "Process Improvements for the Genome Sequencer 20," 2006, Advances in Genome Biology and Technology, 2006 (Year: 2006).*

*Primary Examiner* — Kevin Joyner
*Assistant Examiner* — Holly M Mull
(74) *Attorney, Agent, or Firm* — Brinks Gilson & Lione

(57) ABSTRACT

Disclosed is a specimen processing apparatus for genetic testing. The apparatus includes: a mode setting section configured to receive a setting of an operation mode from: an emulsion preparation mode for preparing a water-in-oil type (W/O type) emulsion having dispersed therein a plurality of droplets, each droplet containing a specimen which contains DNA and a bead to which a reagent component necessary for amplifying a target DNA molecule is bound; and an emulsion breaking mode for breaking the emulsion and collecting beads from the droplets; and a controller programmed to control the transfer unit and the dispensing unit in accordance with the operation mode set by the mode setting section.

20 Claims, 28 Drawing Sheets

(51) Int. Cl.
*C12Q 1/68* (2018.01)
*B01L 3/00* (2006.01)
*G01N 35/00* (2006.01)
B01L 7/00 (2006.01)
B01L 9/00 (2006.01)

(52) U.S. Cl.
CPC . *B01L 2300/021* (2013.01); *B01L 2300/0829* (2013.01); *B01L 2400/043* (2013.01)

(56) References Cited

U.S. PATENT DOCUMENTS

| | | |
|---|---|---|
| 2004/0208795 A1 | 10/2004 | Toi et al. |
| 2005/0064460 A1 | 3/2005 | Holliger et al. |
| 2005/0227264 A1 | 10/2005 | Nobile et al. |
| 2010/0111384 A1* | 5/2010 | Nagai ................ G01N 35/1011 382/128 |
| 2012/0183967 A1 | 7/2012 | Dressman et al. |
| 2013/0209995 A1 | 8/2013 | Andrulat et al. |
| 2013/0225445 A1 | 8/2013 | Seo et al. |
| 2013/0288873 A1* | 10/2013 | Barbee .................... B04B 13/00 494/9 |
| 2015/0056663 A1* | 2/2015 | Tajima ...................... B01L 7/52 435/91.2 |
| 2016/0319329 A1* | 11/2016 | Natale ................. G01N 35/028 |

\* cited by examiner

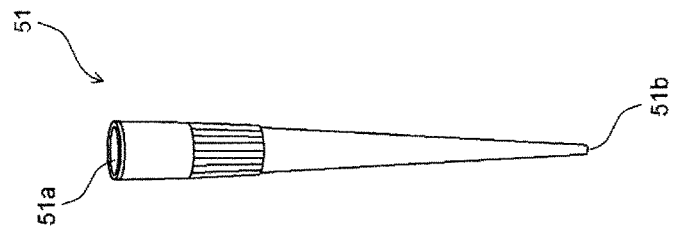
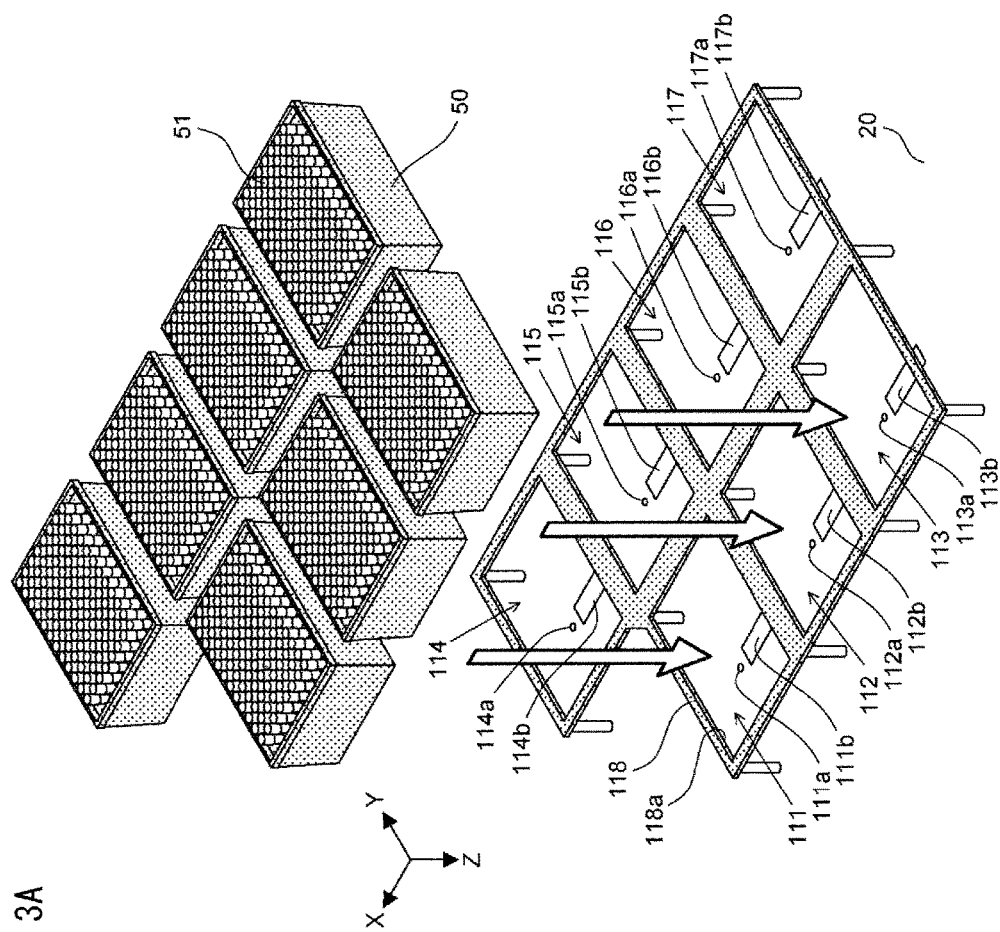

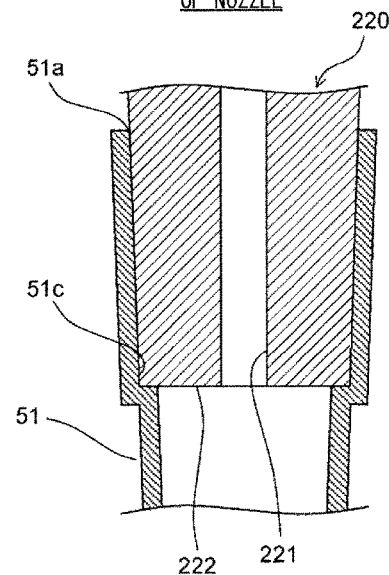
FIG. 10A COMPARATIVE EXAMPLE 1 OF NOZZLE
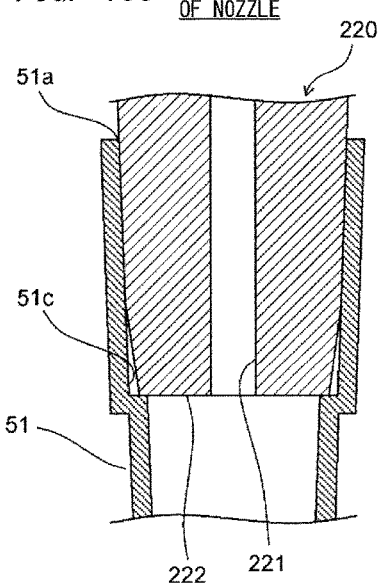
FIG. 10C COMPARATIVE EXAMPLE 2 OF NOZZLE
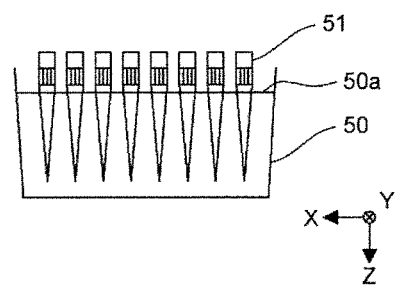
FIG. 10B
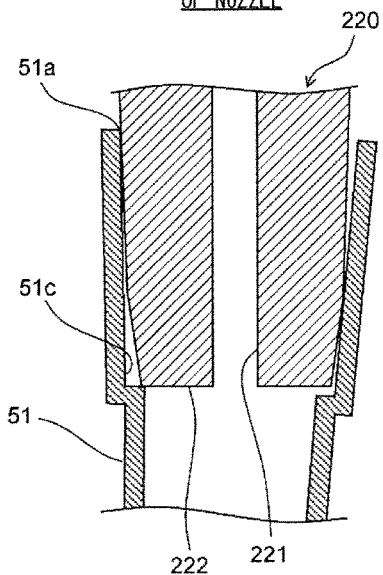
FIG. 10E COMPARATIVE EXAMPLE 2 OF NOZZLE
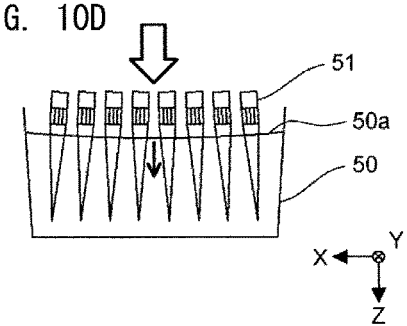
FIG. 10D

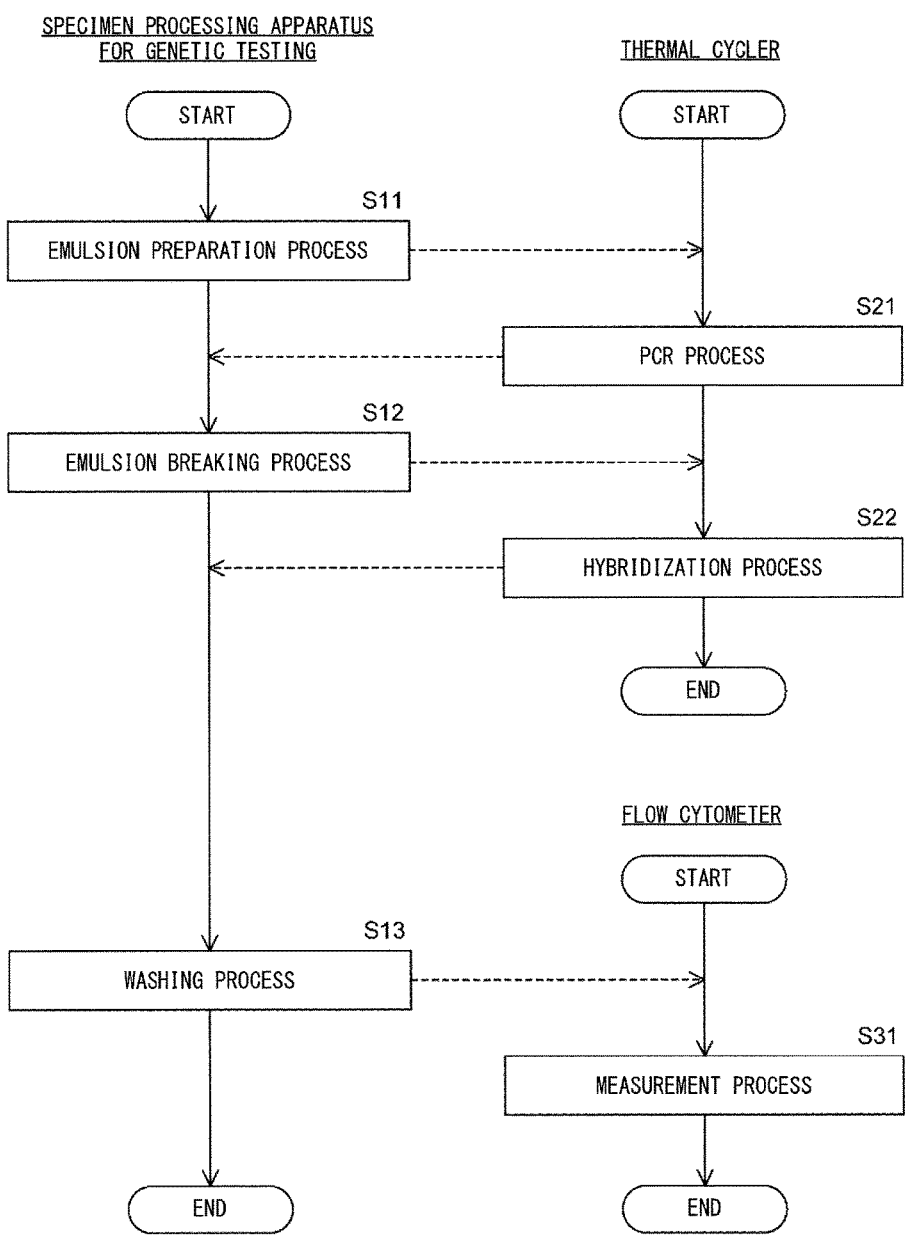

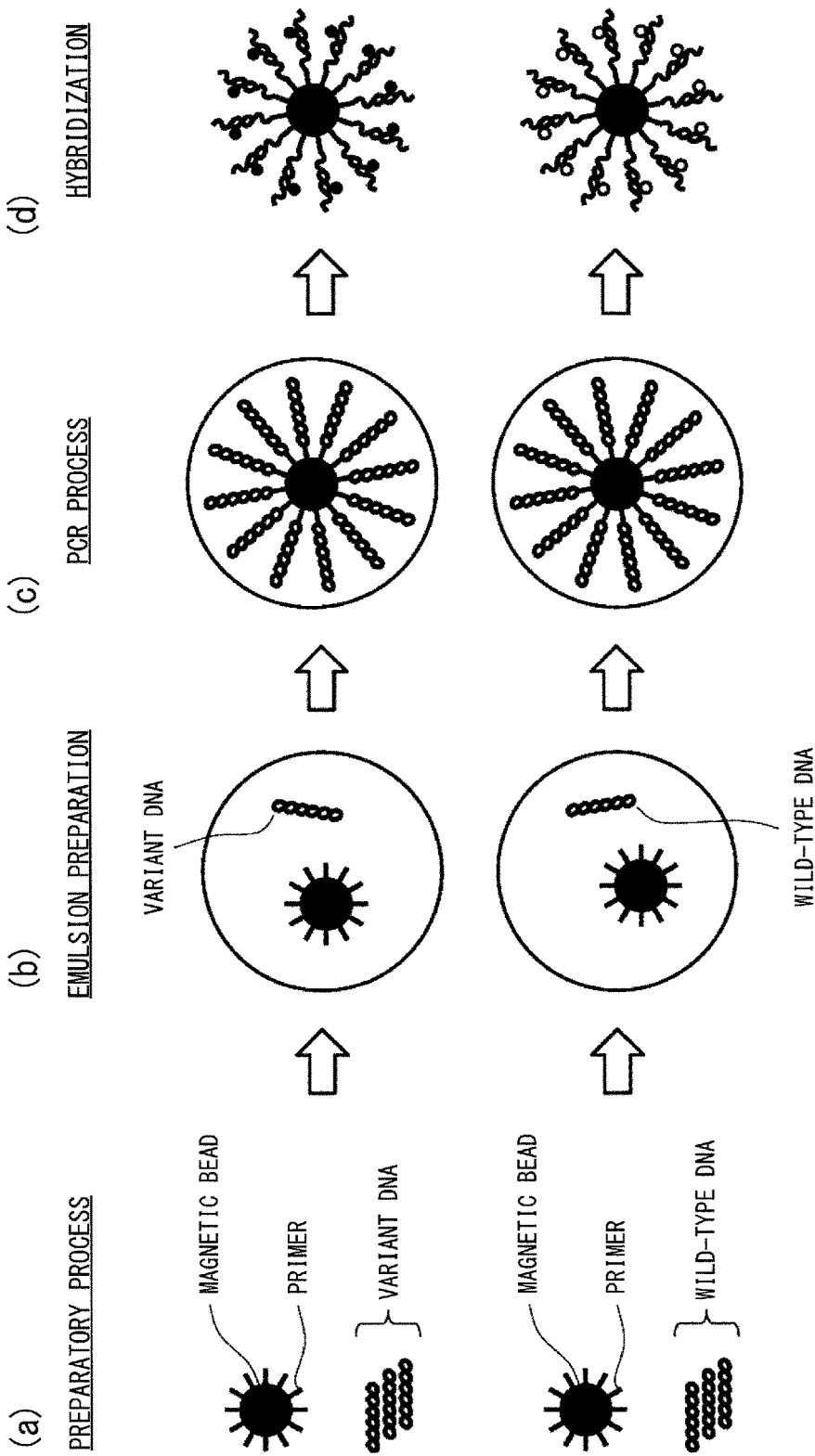

FIG. 16

| | EMULSION PREPARATION MODE | | | | | | | | | | | | EMULSION BREAKING MODE | | | | | | | | | | | | WASH MODE | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 1 | 2 | 3 | 4 | 5 | 6 | 7 | 8 | 9 | 10 | 11 | 12 | 1 | 2 | 3 | 4 | 5 | 6 | 7 | 8 | 9 | 10 | 11 | 12 |
| 111a | | | | | | ○ | | | | | | | ○ | | | | | | | | | | | | ○ | ○ | ○ | ○ | ○ | ○ | ○ | ○ | ○ | ○ | ○ | ○ |
| 112a | | | | | | | | | | | | | | ○ | ○ | | | | | | | | | | | ○ | ○ | ○ | ○ | ○ | ○ | ○ | ○ | ○ | ○ | ○ |
| 113a | | | | | | | | | | | | | | ○ | ○ | ○ | ○ | ○ | ○ | | | | | | | | ○ | ○ | ○ | ○ | ○ | ○ | ○ | ○ | ○ | ○ |
| 114a | | | | | | | | | | | | | | | | ○ | ○ | ○ | ○ | ○ | | | | | | | | ○ | ○ | ○ | ○ | ○ | ○ | ○ | ○ | ○ |
| 115a | | | | | | | | | | | | | | | | | ○ | ○ | ○ | ○ | ○ | | | | | | | | | ○ | ○ | ○ | ○ | ○ | ○ |
| 116a | | | | | | | | | | | | | | | | | | ○ | ○ | ○ | ○ | ○ | | | | | | | | | | ○ | ○ | ○ | ○ | ○ |
| 117a | | | | | | | | | | | | | | | | | | | ○ | ○ | ○ | ○ | ○ | ○ | | | | | | | | | | | | |
| 121a | | | | | | ○ | | | | | | | | | | | | ○ | | | | | | | | | | | | ○ | | | | | | |
| 131a | | | | | | ○ | | | | | | | | | | | | ○ | | | | | | | | | | | | ○ | | | | | | |
| 132a | | | | | | ○ | | | | | | | | | | | | | ○ | | | | | | | | | | | | | | | | | |
| 132b | | | | | | | | | | | | | | | | | | | ○ | | | | | | | | | | | | | | | | | |
| 132c | | | | | | | | | | | | | | | | | | ○ | | | | | | | | | | | | ○ | | | | | | |
| 133a | | | | | | | | | | | | | | | | | | ○ | | | | | | | | | | | | | | | | | | |
| 141a | | | | | | | | | | | | | | | | | | ○ | | | | | | | | | | | | | | | | | | |

# SPECIMEN PROCESSING APPARATUS FOR GENETIC TESTING

CROSS REFERENCE TO RELATED APPLICATIONS

This application claims priority from prior Japanese Patent Application No. 2015-132131, filed on Jun. 30, 2015, entitled "SPECIMEN PROCESSING APPARATUS FOR GENETIC TESTING", the entire content of which is incorporated herein by reference.

FIELD OF THE INVENTION

The present invention relates to a specimen processing apparatus for genetic testing.

BACKGROUND

Conventionally, for nucleic acid sequence determination, gene mutation detection, and the like, a technique has been used in which: nucleic acid molecules are amplified in droplets of a "water-in-oil type" emulsion; the amplification product is fixed on the surface of beads; the beads are collected by breaking the droplets of the emulsion; and then the amplification product is analyzed.

For example, U.S. Patent application Publication No. 2012/183967 discloses a method for detecting gene mutation by the BEAMing method. In the detection method according to U.S. Patent application Publication No. 2012/183967, the steps of binding oligonucleotides to beads (step 1), preparing a microemulsion (step 2), PCR cycling (step 3), magnetic capture of beads (step 4), sequence differentiation (step 5), and flow cytometry (step 6) are performed, and then, mutant DNA molecules are counted.

In the preparation of the microemulsion (step 2), an aqueous phase that contains magnetic beads and a target gene, and an oil phase that contains a reagent for preparing an emulsion are mixed together and stirred, whereby the microemulsion is prepared. With the technique according to U.S. Patent application Publication No. 2012/183967, 200 microliters of the aqueous phase is added by a dropping method to 400 microliters of the oil phase, whereby a water-in-oil type microemulsion is prepared. The addition of the aqueous phase by the dropping method is performed for about one minute while the mixture is being stirred with a stirrer at 1400 RPM. Then, the mixture is further stirred for 30 minutes.

In the magnetic capture of beads (step 4), in order to break the microemulsion, an NX buffer is added to the microemulsion. After the solution is stirred, the oil phase is separated from the aqueous phase by centrifugation, and the top oil phase is removed. To the resultant aqueous phase, the NX buffer is added, and the oil phase is removed by centrifugation once again. Then, the magnetic beads are attracted by a magnet, and the supernatant is carefully removed using a pipette. Further, the magnetic beads are washed with a PCR buffer three times using magnetic separation, and finally re-suspended in the PCR buffer. In this manner, in step 4, in order to break the microemulsion, operations of removal of the oil phase, magnetic separation, and the like are performed a plurality of times.

SUMMARY OF THE INVENTION

The scope of the present invention is defined solely by the appended claims, and is not affected to any degree by the statements within this summary.

As described above, since the emulsion preparation step and the emulsion breaking step are complicated, an experienced laboratory technician or the like is required to manually perform these steps, or detailed condition information is required to be inputted in order to cause a commercial liquid handler to execute these operations.

A first aspect of the present invention relates to a specimen processing apparatus for genetic testing. The specimen processing apparatus includes: a dispensing-tip-container placement part in which a dispensing-tip-container having a plurality of dispensing tips rested thereon is placed; a reagent-container placement part in which a reagent container holding a reagent is placed; a microplate placement part in which a microplate having a plurality of wells is placed; a dispensing unit configured to aspirate and discharge a liquid with a dispensing tip attached thereto; a transfer unit configured to move the dispensing unit to the dispensing-tip-container placement part, the reagent-container placement part, and the microplate placement part; a mode setting section configured to receive a setting of an operation mode from: an emulsion preparation mode for preparing a water-in-oil type (W/O type) emulsion having dispersed therein a plurality of droplets, each droplet containing a specimen which contains DNA and a bead to which a reagent component necessary for amplifying a target DNA molecule is bound; and an emulsion breaking mode for breaking the emulsion and collecting beads from the droplets; and a controller programmed to control the transfer unit and the dispensing unit in accordance with the operation mode set by the mode setting section.

A second aspect according to the present invention relates to a specimen processing apparatus for genetic testing. The specimen processing apparatus includes: a dispensing-tip-container placement part in which a dispensing-tip-container having a plurality of dispensing tips rested thereon is placed; a reagent-container placement part in which a reagent container holding a reagent is placed; a microplate placement part in which a microplate having a plurality of wells is placed; a dispensing unit configured to aspirate and discharge a liquid with a dispensing tip attached thereto; a transfer unit configured to move the dispensing unit to the dispensing-tip-container placement part, the reagent-container placement part, and the microplate placement part; a mode setting section configured to receive a setting of an emulsion breaking mode for breaking a water-in-oil type (W/O type) emulsion having dispersed therein a plurality of droplets, each droplet containing a specimen which contains DNA and a bead to which a reagent component necessary for amplifying a target DNA molecule is bound, the emulsion breaking mode being for collecting beads from the droplets; and a controller programmed to control the transfer unit and the dispensing unit in accordance with the emulsion breaking mode set by the mode setting section.

BRIEF DESCRIPTION OF THE DRAWINGS

FIG. 3A shows dispensing-tip-containers to be respectively placed in dispensing-tip-container placement parts according to Embodiment 1;

FIG. 3B shows a configuration of a dispensing tip according to Embodiment 1;

FIG. 10A shows a cross section of a nozzle according to Comparative Example 1, viewed from the lateral surface direction;

FIG. 10B shows a state in which a placement surface of the dispensing-tip-container is parallel to a horizontal plane;

FIG. 10C shows a cross section of a nozzle according to Comparative Example 2, viewed from the lateral surface direction;

FIG. 10D shows a state in which the placement surface of the dispensing-tip-container has flexed;

FIG. 10E shows a state in which the dispensing tip is attached in a tilted manner to the nozzle according to Comparative Example 2;

FIG. 13 is a flow chart showing a flow of genetic testing by a BEAMing method that uses the specimen processing apparatus for genetic testing according to Embodiment 1;

FIG. 14 schematically shows intermediate states of the genetic testing according to Embodiment 1;

FIG. 16 shows the lighting states of light-emitters according to Embodiment 1 at the time when the operation mode and the number of columns to be processed are set;

DETAILED DESCRIPTION OF THE PREFERRED EMBODIMENTS

Embodiment 1

Embodiment 1 can be applied to an apparatus for performing specimen pretreatment for genetic testing that uses an emulsion. In particular, Embodiment 1 can be applied to an apparatus for performing pretreatment on a specimen for genetic testing when gene is to be detected according to the BEAMing (Bead, Emulsion, Amplification, and Magnetics) method. The BEAMing method is gene analyzing technology realized by combining digital PCR technology and flow cytometry technology. The digital PCR is a measurement technique for performing absolute quantification of the target gene concentration in a sample, by dispersing sample DNA diluted to a limiting dilution (a dilution that causes 1 or 0 target DNA molecule to be contained each micro partition) into micro partitions to perform PCR amplification, and then, by directly counting the number of micro partitions having positive amplification signals. In a micro partition that contains the target gene, the amplification signal becomes positive. In a micro partition that does not contain the target gene or that does not contain the sample DNA itself, the amplification signal becomes negative.

The BEAMing method includes, for example, a DNA extraction process, a dilution process, an emulsion preparation process, a PCR process, an emulsion breaking process, a hybridization process, a washing process, a measurement process by a flow cytometer, and the like. Among these, the apparatus according to Embodiment 1 performs the emulsion preparation process, the emulsion breaking process, and the washing process.

Figure 1A:
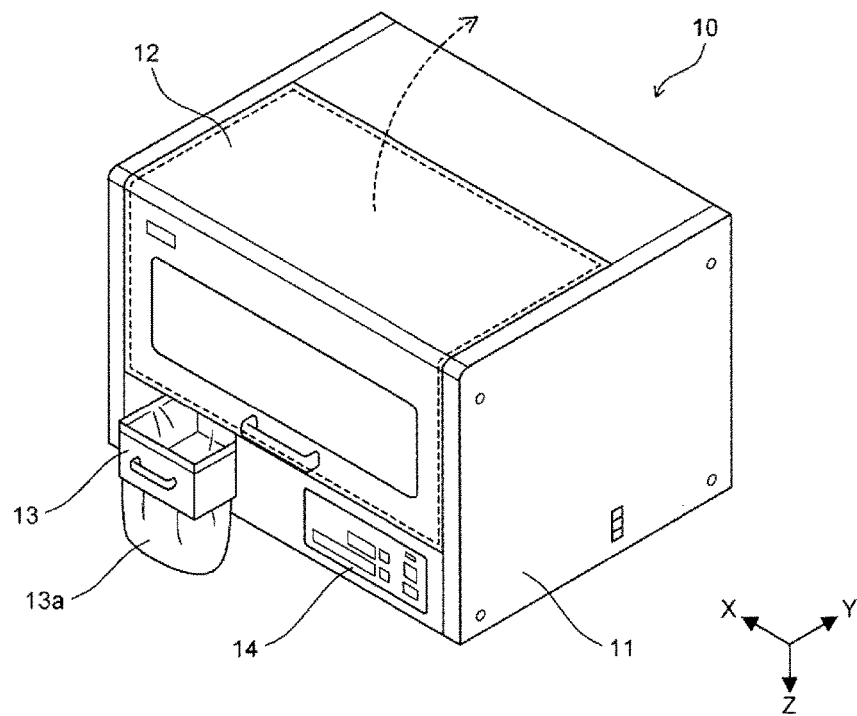
FIG. 1A shows an external appearance of a specimen processing apparatus for genetic testing according to Embodiment 1.

As shown in FIG. 1A, a specimen processing apparatus 10 for genetic testing includes a housing 11, a cover 12, a dispensing tip disposal part 13, and an operation part 14. In FIG. 1A, the XYZ axes are orthogonal to one another. Viewed from the apparatus front face provided with the operation part 14, the X-axis positive direction is the leftward direction, the Y-axis positive direction is the rearward direction, and the Z-axis positive direction is the vertically downward direction. Also in the following drawings, the XYZ axes are the same as the XYZ axes shown in FIG. 1A.

An operator can access the inside of the housing 11, by moving the cover 12 indicated with a broken line into a direction indicated with a broken line arrow to open the housing 11. A disposal bag 13a is set to the dispensing tip disposal part 13. As described later, dispensing tips 51 that have been used are discarded into the disposal bag 13a. With respect to the dispensing tip disposal part 13, a portion thereof on the Y-axis positive side is located inside the housing 11 relative to the cover 12. Through the portion, of the dispensing tip disposal part 13, that is located inside the housing 11, dispensing tips 51 that have been used are discarded into the disposal bag 13a.

Figure 1B:
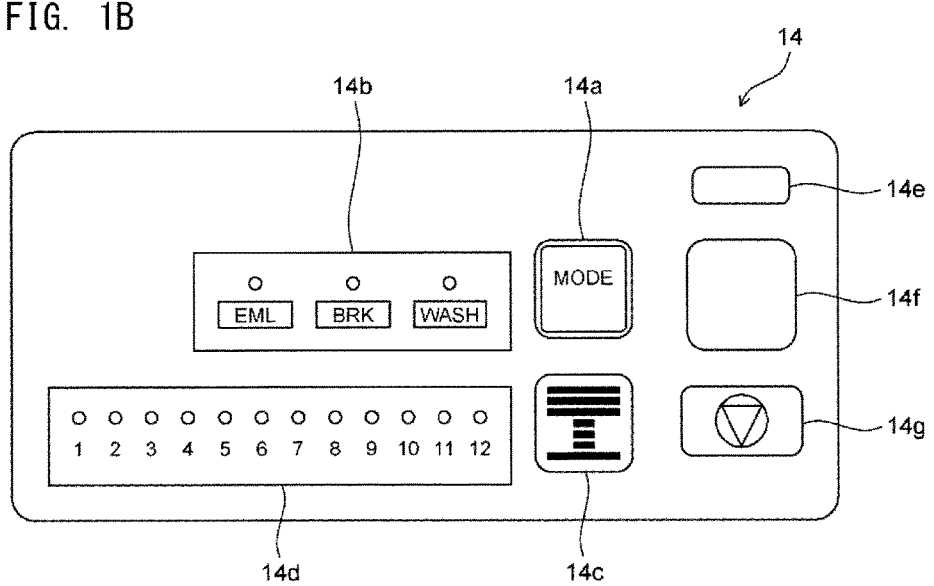
FIG. 1B shows a configuration of a mode setting section according to Embodiment 1.

As shown in FIG. 1B, the operation part 14 includes a mode setting section 14a, a mode indication section 14b, a target well setting section 14c, a target well indication section 14d, an apparatus state indication section 14e, a start instruction section 14f, and a stop instruction section 14g.

The mode setting section 14a is a button for setting an operation mode of the specimen processing apparatus 10 for genetic testing. Every time pressing the mode setting section 14a once, the operator can cyclically switch the operation mode in the order of an emulsion preparation mode, an emulsion breaking mode, and a wash mode. The mode indication section 14b includes three light-emitters which respectively correspond to the three operation modes. Each of these light-emitters is implemented by an LED. When an operation mode is set by the mode setting section 14a, the light-emitter in the mode indication section 14b corresponding to the set operation mode is lit.

The target well setting section 14c is a button for setting the number of columns of wells 61a to be processed among a plurality of wells 61a provided in a microplate 61 described later. Every time pressing the target well setting section 14c once, the operator can switch the number of process columns in the order of column 1 to column 12. The target well indication section 14d includes 12 light-emitters each indicating the number of process columns. Each of these light-emitters is implemented by an LED. When the number of process columns is set by the target well setting section 14c, the light-emitter(s) corresponding to the set number of process columns is(are) lit. For example, when the number of process columns is set to 7, the light-emitters of the target well indication section 14d corresponding to column 1 to column 7 are lit.

The apparatus state indication section 14e is a light-emitter that indicates the state of the specimen processing apparatus 10. This light-emitter is implemented by an LED. When the specimen processing apparatus 10 is in a standby state, the apparatus state indication section 14e is lit green. The standby state is a state in which the emulsion preparation process, the emulsion breaking process, and the washing process which are described later are not being performed, and in which these processes can be started. While the specimen processing apparatus 10 is in an initialization process or in operation, the apparatus state indication section 14e blinks green. While an error has occurred in the specimen processing apparatus 10, the apparatus state indication section 14e is lit red. While the power supply of the specimen processing apparatus 10 is in an OFF state, or until about one minute elapses after the power supply of the specimen processing apparatus 10 has been turned on, the apparatus state indication section 14e is not lit. When about one minute has elapsed after the power supply had been turned on, and when any of the emulsion preparation process, the emulsion breaking process, and the washing process has ended, the specimen processing apparatus 10 enters the standby state.

The start instruction section 14f is a button for starting the process to be performed by the specimen processing apparatus 10. By pressing the start instruction section 14f in the standby state, the operator can cause the specimen processing apparatus 10 to start the process in the operation mode set by the mode setting section 14a. The stop instruction section 14g is a button for stopping the process performed by the specimen processing apparatus 10.

Figure 2:
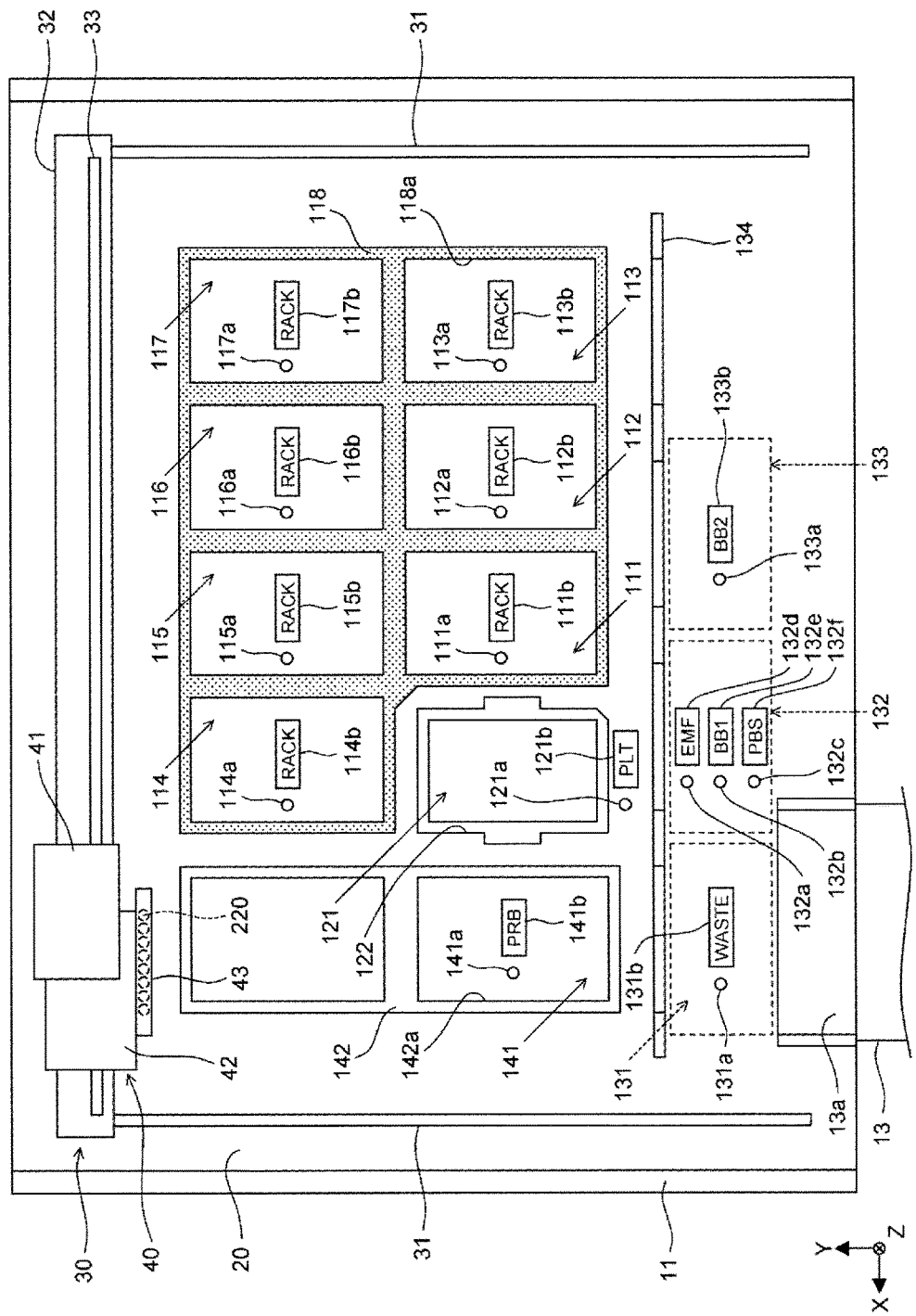
FIG. 2 is a schematic diagram of the inside of a housing of the specimen processing apparatus for genetic testing according to Embodiment 1, viewed from above.

As shown in FIG. 2, inside the housing 11, the specimen processing apparatus 10 includes a bottom surface 20, a transfer unit 30, a dispensing unit 40, dispensing-tip-container placement parts 111 to 117, a microplate placement part 121, and reagent-container placement parts 131 to 133 and 141.

The transfer unit 30 causes the dispensing unit 40 to be moved to the dispensing-tip-container placement parts 111 to 117, the microplate placement part 121, and the reagent-container placement parts 131 to 133 and 141. The transfer unit 30 includes two rails 31, a forward-rearward movement member 32, and a rail 33. The two rails 31 extend in the front-rear direction. The forward-rearward movement member 32 and the rail 33 extend in the left-right direction. The forward-rearward movement member 32 is configured to be movable in the front-rear direction along the two rails 31. The rail 33 is provided on the forward-rearward movement member 32. The transfer unit 30 further includes a forward-rearward drive unit and a leftward-rightward drive unit which are not shown. The transfer unit 30 causes the forward-rearward movement member 32 to move in the front-rear direction along the two rails 31, by means of the forward-rearward drive unit. The transfer unit 30 causes the dispensing unit 40 to move in the left-right direction along the rail 33, by means of the leftward-rightward drive unit.

The dispensing unit 40 has dispensing tips 51 described later attached thereto, and performs aspiration and discharge of a liquid. The dispensing unit 40 includes a first drive mechanism 41, a second drive mechanism 42, and an aspiration/discharge unit 43. The dispensing unit 40 is configured to be movable in the left-right direction along the rail 33. The first drive mechanism 41 causes the second drive mechanism 42 and the aspiration/discharge unit 43 to move in the vertical direction along a rail not shown extending in the vertical direction. The second drive mechanism 42 causes cylinders 212 described later to move in the vertical direction. By the cylinders 212 being raised/lowered, aspiration and discharge are performed through dispensing tips 51 respectively attached to eight nozzles 220 of the aspiration/discharge unit 43. The eight nozzles 220 are arranged in the X-axis direction at a predetermined interval. The configurations of the second drive mechanism 42 and the aspiration/discharge unit 43 will be described later with reference to FIG. 7 to FIG. 11B.

As shown in FIG. 3A, dispensing tip containers 50 are placed in the dispensing-tip-container placement parts 111 to 117, respectively. 96 dispensing tips 51 are rested on one dispensing tip container 50. The 96 dispensing tips 51 are in an arrangement of 12 in the front-rear direction and 8 in the left-right direction. The eight dispensing tips 51 rested in the left-right direction in the dispensing tip container 50 are arranged at an interval identical to that of the eight nozzles 220. As shown in FIG. 3B, an opening 51a and a lower end 51b are formed in each dispensing tip 51. The nozzle 220 is fitted into the opening 51a. The lower end 51b is provided with a hole for performing aspiration and discharge therethrough.

As shown in FIG. 2 and FIG. 3A, the dispensing-tip-container placement parts 111 to 117 are formed by the bottom surface 20 and seven openings 118a of a frame member 118 provided on the bottom surface 20. The seven openings 118a each have a border into which a dispensing tip container 50 is fitted.

On the bottom surface 20 in the dispensing-tip-container placement parts 111 to 117, light-emitters 111a to 117a are provided, respectively. Each of the light-emitters 111a to 117a is implemented by an LED. The light-emitter 111a to 117a is lit when it is necessary to set the dispensing tip container 50 into its corresponding dispensing-tip-container placement part 111 to 117. For example, when it is necessary to set the dispensing tip containers 50 into the dispensing-tip-container placement parts 111 to 115, respectively, the light-emitters 111a to 115a are lit, and the light-emitters 116a and 117a are not lit. It should be noted that each of the dispensing tip containers 50 set in the dispensing-tip-container placement parts 111 to 117 is assumed to always have 96 dispensing tips 51 rested thereon.

Labels 111b to 117b are affixed at positions on the bottom surface 20 that are adjacent to the light-emitters 111a to 117a, respectively. As shown in FIG. 2, the labels 111b to 117b each have an indication "RACK" which indicates that the kind of the containers that should be placed in the dispensing-tip-container placement parts 111 to 117 is the dispensing tip container 50. In FIG. 3A, the characters in the labels 111b to 117b are not shown for convenience.

Instead of the labels 111b to 117b, liquid crystal display sections may be provided. On each liquid crystal display section, "RACK" indicating the kind of the container that should be placed is displayed. In this case, the light-emitters 111a to 117a are omitted, and back lights of the liquid crystal display sections may function as the light-emitters. For example, only the liquid crystal display sections of the dispensing-tip-container placement parts 111 to 117 into which the dispensing tip containers 50 need to be set operate, and the back lights of these liquid crystal display sections are lit.

Labels 121b, 131b, 132d to 132f, 133b, and 141b which are described later may also be replaced with liquid crystal display sections. Also on each of these liquid crystal display sections, the kind of the container that should be placed is indicated. In this manner, if the liquid crystal display section is provided instead of each label, even when the kind of the container that should be placed is changed, the kind of the container that should be placed can be indicated only by changing the display content of the liquid crystal display section.

As shown in FIG. 3A, as indicated by the white arrows, the operator sets the dispensing tip containers 50 on the dispensing-tip-container placement parts 111 to 117, respectively. When a dispensing tip container 50 is set on a dispensing-tip-container placement part whose light-emitter is lit, the lit light-emitter is hidden by the set dispensing tip container 50. Accordingly, the operator can confirm that the setting of necessary dispensing tip container(s) 50 has been completed.

Here, each dispensing tip container 50 is green, and the frame member 118 is green in accordance with the color of the dispensing tip container 50. Accordingly, the operator can intuitively understand that the setting places of the dispensing tip containers 50 are the dispensing-tip-container placement parts 111 to 117 formed by the frame member 118. In Embodiment 1, only the dispensing tip containers 50 and the dispensing-tip-container placement parts 111 to 117 have the same color with each other, but another type of containers and another placement part may have the same color with each other so as to allow intuitive recognition of the setting place thereof.

Figure 4A:
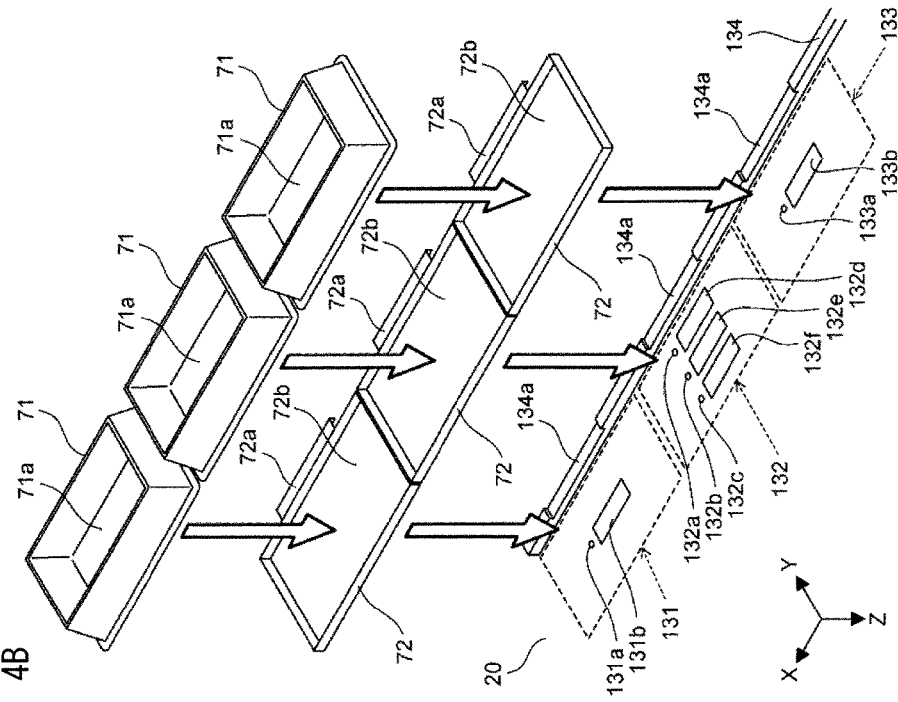
FIG. 4A shows a microplate to be placed in a microplate placement part and a reagent container to be placed in a reagent-container placement part according to Embodiment 1.

As shown in FIG. 4A, the microplate 61 is placed in the microplate placement part 121. The microplate 61 has a plurality of wells 61a each having a concave shape. On the microplate 61, the plurality of wells 61a are provided, with an interval therebetween, in a plurality of rows and a plurality of columns. Specifically, a total of 96 wells 61a are provided such that 12 wells 61a are arranged in the front-rear direction and 8 wells 61a are arranged in the left-right direction on the top surface of the microplate 61. The eight wells 61a in the left-right direction are arranged at an interval identical to that of the eight nozzles 220. Each well 61a holds the target DNA molecules and the like. The microplate 61 has a contour having a cutout 61b at the end thereof on the X-axis negative side and the Y-axis negative side. A flange portion extending downward is formed along the entire periphery of the microplate 61, and this flange portion forms the peripheral lateral surface of the microplate 61. The flange portion has the same width and the same thickness along the entire periphery of the microplate 61.

As shown in FIG. 2 and FIG. 4A, the microplate placement part 121 is formed by a recessed part 122 provided in the bottom surface 20. The recessed part 122 has a border into which the microplate 61 is fitted.

The recessed part 122 has a bottom surface 122a, an opening 122b, and a protruding portion 122c. The bottom surface 122a is at a level lower than the bottom surface 20. The bottom surface 122a supports the flange portion at the periphery of the microplate 61 set in the microplate placement part 121. The opening 122b is provided at the center of the bottom surface 122a. The border of the opening 122b is set to be larger than the contour outside the 96 wells 61a at the time when the microplate 61 is set in the microplate placement part 121. Through the opening 122b, magnetic force from magnet members 80 described later is applied to the wells 61a. The magnet members 80 will be described later with reference to FIGS. 6A and 6B.

The protruding portion 122c is provided at a position corresponding to the cutout 61b at the time when the microplate 61 is appropriately set in the microplate placement part 121. In other words, the microplate placement part 121 has a border to which the cutout 61b of the microplate 61 is fitted. Accordingly, the microplate 61 can be prevented from being set in a wrong orientation onto the microplate placement part 121. Alternatively, a protruding portion may be provided in microplate 61, and a cutout may be provided in the recessed part 122. Also in this case, the microplate 61 can be prevented from being set in a wrong orientation onto the microplate placement part 121.

On the bottom surface 20 to the front of the microplate placement part 121, a light-emitter 121a and a label 121b are provided. The light-emitter 121a is implemented by an LED. The light-emitter 121a is lit when it is necessary to set the microplate 61 into the microplate placement part 121. The label 121b is affixed at a position on the bottom surface 20 that is adjacent to the light-emitter 121a. The label 121b has an indication "PLT" which indicates that the kind of the container that should be set in the microplate placement part 121 is the microplate 61. In FIG. 4A, the characters in the label 121b are not shown for convenience.

As shown in FIG. 4A, as indicated by the white arrow, the operator sets the microplate 61 in the microplate placement part 121. It should be noted that the light-emitter 121a and the label 121b may be provided below the opening 122b. In such a case, similarly to the light-emitters in other placement parts, the light-emitter 121a is hidden by the microplate 61 when the microplate 61 is set in the microplate placement part 121.

Then, as shown in FIG. 4A, a reagent container 62 is placed in a reagent-container placement part 141. The reagent container 62 has a similar configuration as that of the microplate 61. That is, the reagent container 62 has a plurality of reagent holding portion 62a each having a concave shape. A total of 96 reagent holding portions 62a are provided such that 12 reagent holding portions 62a are arranged in the front-rear direction and 8 reagent holding portions 62a are arranged in the left-right direction on the top surface of the reagent container 62. The eight reagent holding portions 62a in the left-right direction are arranged at an interval identical to that of the eight nozzles 220. Each reagent holding portion 62a holds a reagent containing a labeled probe that can be hybridized to an amplified target DNA molecule. The reagent container 62 has a contour having a cutout 62b at the end thereof on the X-axis negative side and the Y-axis negative side.

As shown in FIG. 2 and FIG. 4A, the reagent-container placement part 141 is formed by a frame member 142 provided on the bottom surface 20. The frame member 142 has an opening 142a of a rectangular shape. An adaptor 63 is placed in the opening 142a. The lower part of the adaptor 63 has a contour that fits in the opening 142a of the frame member 142. The adaptor 63 is detachable from the opening 142a. In an ordinary use form, the adaptor 63 is placed in the opening 142a in advance.

The adaptor 63 has an opening 63a passing therethrough in the up-down direction. The upper part of the adaptor 63 has a contour that fits inside the peripheral lateral surface of the reagent container 62. The upper part of the adaptor 63 has a cutout 63b. The cutout 63b is provided at a position that corresponds to the cutout 62b at the time when the reagent container 62 is appropriately set in the adaptor 63. Here, the adaptor 63 has been placed in the opening 142a of the frame member 142, in a state where the cutout 63b is located at the front right side. Accordingly, the reagent container 62 can be prevented from being set in a wrong orientation onto the reagent-container placement part 141. A protruding portion may be provided in each of the reagent container 62 and the adaptor 63, such that the reagent container 62 can be fitted in the adaptor 63.

On the bottom surface 20 of the reagent-container placement part 141, a light-emitter 141a and a label 141b are provided. The light-emitter 141a is implemented by an LED. The light-emitter 141a is lit when it is necessary to set the reagent container 62 into the reagent-container placement part 141. The label 141b is affixed at a position on the bottom surface 20 that is adjacent to the light-emitter 141a. The label 141b has an indication "PRB" which indicates that the kind of the container that should be placed in the reagent-container placement part 141 is the reagent container 62. In FIG. 4A, the characters in the label 141b are not shown for convenience.

As shown in FIG. 4A, as indicated by the white arrows, the operator sets the reagent container 62 into the adaptor 63, in a state where the adaptor 63 is placed in the opening 142a. Accordingly, the reagent container 62 is set in the reagent-container placement part 141. When the reagent container 62 is set in the reagent-container placement part 141 while the light-emitter 141a is lit, the lit light-emitter 141a is hidden by the set reagent container 62. Accordingly, the operator can confirm that the setting operation of the reagent container 62 has been completed.

Figure 4B:
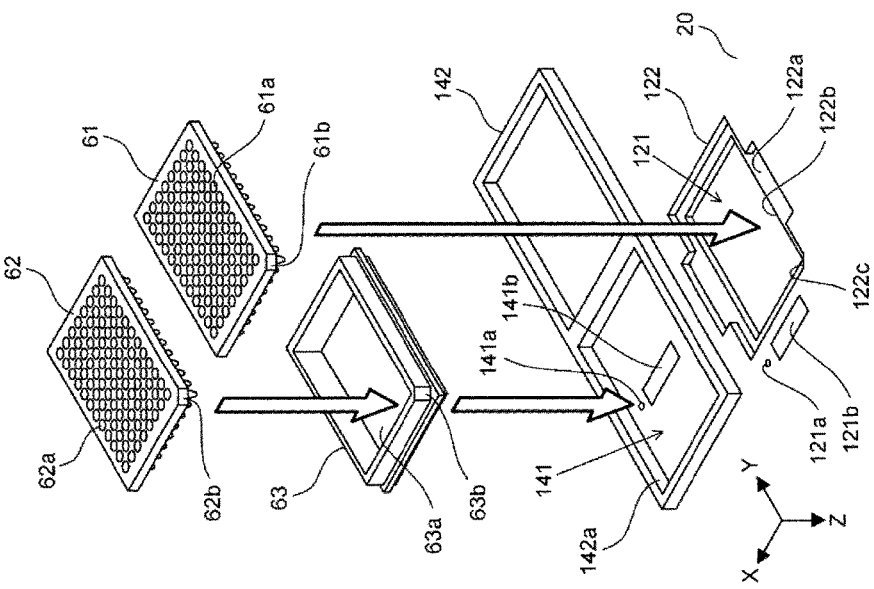
FIG. 4B shows reagent containers to be respectively placed in reagent-container placement parts according to Embodiment 1.

As shown in FIG. 4B, a reagent container 71 is placed in each of the reagent-container placement parts 131 to 133. Each reagent container 71 has a substantially rectangular contour in a plan view, and a substantially trapezoidal contour in a side view. An empty reagent container 71 for holding waste liquid is placed in the reagent-container placement part 131. A reagent container 71 that holds an emulsion reagent, a first breaking reagent, or a phosphate buffered saline is placed in reagent-container placement part 132. Hereinafter, the phosphate buffered saline will be referred to as "PBS". A reagent container 71 that holds a second breaking reagent is placed in the reagent-container placement part 133. In each reagent container 71, a recessed part 71a for holding a liquid is formed. The length in the X-axis direction of the recessed part 71a is greater than the length in the X-axis direction that corresponds to the eight nozzles 220.

The emulsion reagent is a reagent for forming an oil phase in an aqueous phase which contains magnetic beads to each of which a plurality of primer molecules for amplifying the target DNA molecule are bound. The emulsion reagent includes a silicone emulsifier, an oil, and the like. Each of the first and second breaking reagents is a breaking reagent for breaking a water-in-oil type (W/O type) emulsion having been subjected to PCR. The first and second breaking reagents each include an alcohol, a surfactant, and the like. In order to break the droplets, the amount of the alcohol included in the first breaking reagent is set to be greater than that in the second breaking reagent. In order to adjust the state of the target DNA molecule, the amount of the alcohol included in the second breaking reagent is set to be smaller than that in the first breaking reagent. The PBS is a reagent used in the washing process described later.

As shown in FIG. 4B, the reagent-container placement parts 131 to 133 are formed by the bottom surface 20 and a bar 134. The bar 134 is provided on the bottom surface 20. The bar 134 has three recessed parts 134a formed therein. An adaptor 72 includes an engagement part 72a and a recessed part 72b. The engagement part 72a is configured to be engaged with the recessed part 134a. The recessed part 72b has a substantially rectangular border into which the bottom of the reagent container 71 is fitted. When the engagement part 72a is engaged with the recessed part 134a of the bar 134, the position at which to set the adaptor 72 on the bottom surface 20 is determined. The reagent container 71 is placed in the recessed part 72b of the adaptor 72 that has been positioned.

On the bottom surface 20 of the reagent-container placement part 131, a light-emitter 131a and the label 131b are provided. On the bottom surface 20 of the reagent-container placement part 132, light-emitters 132a to 132c and the labels 132d to 132f are provided. On the bottom surface 20 of the reagent-container placement part 133, a light-emitter 133a and the label 133b are provided. Each of the light-emitters 131a, 132a to 132c, and 133a is implemented by an LED.

The light-emitter 131a is lit when it is necessary to set an empty reagent container 71 into the reagent-container placement part 131. The light-emitter 132a is lit when it is necessary to set a reagent container 71 that holds the emulsion reagent, into the reagent-container placement part 132. The light-emitter 132b is lit when it is necessary to set a reagent container 71 that holds the first breaking reagent, into the reagent-container placement part 132. The light-emitter 132c is lit when it is necessary to set a reagent container 71 that hold the PBS, into the reagent-container placement part 132. The light-emitter 133a is lit when it is necessary to set a reagent container 71 that holds the second breaking reagent, into the reagent-container placement part 133.

The labels 131b, 132d to 132f, and 133b are affixed at positions on the bottom surface 20 that are adjacent to the light-emitters 131a, 132a to 132c, and 133a, respectively. In FIG. 4B, the characters in the labels 131b, 132d to 132f, and 133b are not shown for convenience.

The label 131b has an indication "WASTE" which indicates that the kind of the container that should be placed in the reagent-container placement part 131 is an empty reagent container 71 for holding waste liquid. The label 132d has an indication "EMF" which indicates that the kind of the container that should be placed in the reagent-container placement part 132 when the light-emitter 132a is lit is a reagent container 71 that holds the emulsion reagent. The label 132e has an indication "BB1" which indicates that the kind of the container that should be placed in the reagent-container placement part 132 when the light-emitter 132b is lit is a reagent container 71 that holds the first breaking reagent. The label 132f has an indication "PBS" which indicates that the kind of the container that should be placed in the reagent-container placement part 132 when the light-emitter 132c is lit is a reagent container 71 that holds the PBS. The label 133b has an indication "BB2" which indicates that the kind of the container that should be placed in the reagent-container placement part 133 is a reagent container 71 that holds the second breaking reagent.

As shown in FIG. 4B, as indicated by the white arrows, the operator places the adaptor 72 such that the engagement part 72a is engaged with the recessed part 134a, and then, sets the reagent container 71 to the reagent-container placement part 131 to 133. When the reagent container 71 is set in the reagent-container placement part whose light-emitter is lit, the lit light-emitter is hidden by the reagent container 71 and the adaptor 72. Accordingly, the operator can confirm that the setting operation of the necessary reagent container 71 has been completed.

Next, a layout for holding the microplate 61 when starting the emulsion preparation process, and a layout for holding the reagent container 62 when starting the emulsion breaking process will be described.

Figure 5:
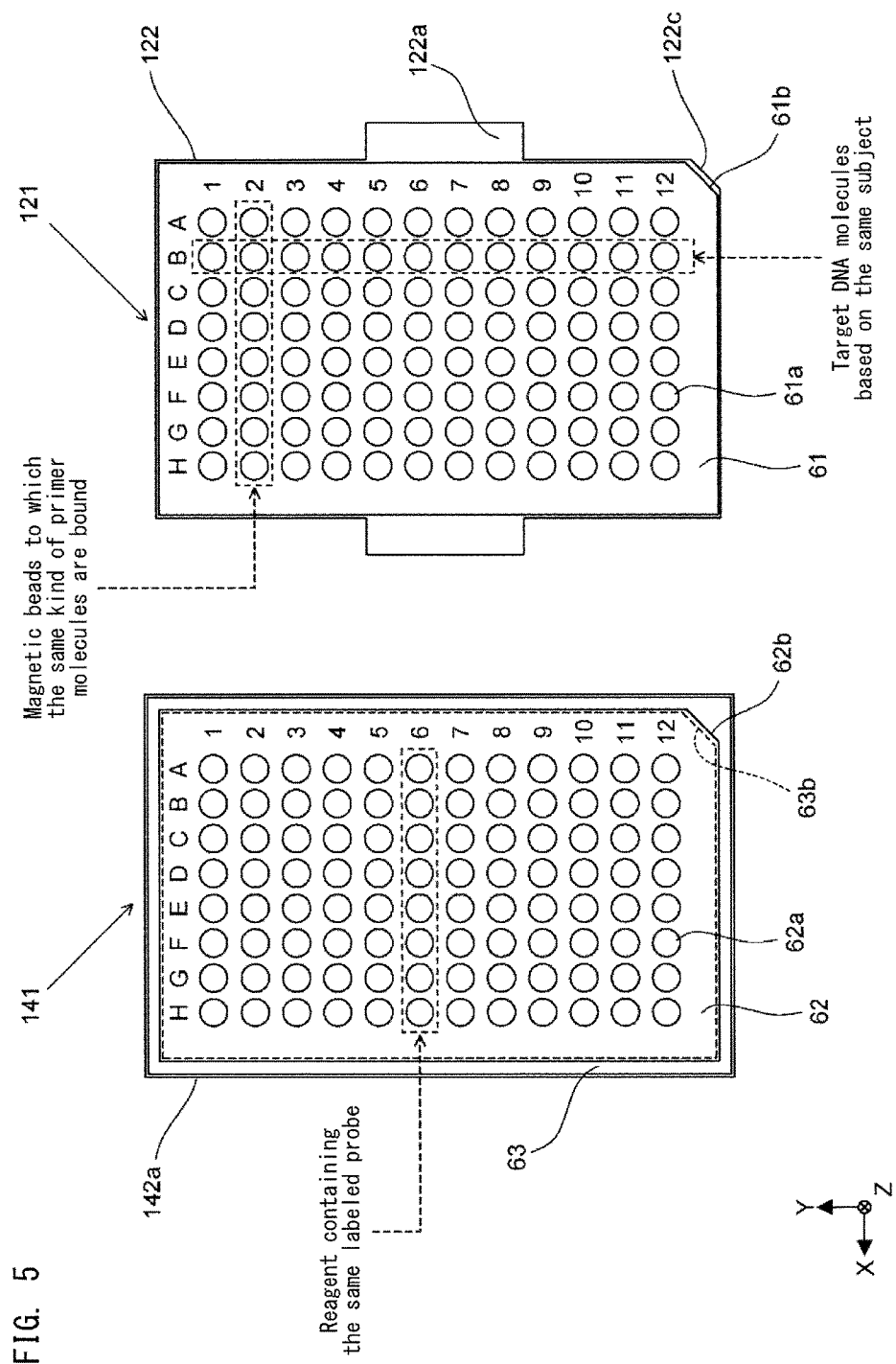
FIG. 5 shows the microplate placed in the microplate placement part and the reagent container placed in the reagent-container placement part according to Embodiment 1.

As shown in FIG. 5, the numerals 1 to 12 indicated on the top surface of each of the microplate 61 and the reagent container 62 represent column numbers, respectively. The characters A to H indicated on the top surface of each of the microplate 61 and the reagent container 62 represent row numbers, respectively. One row corresponds to 12 wells 61a and 12 reagent holding portions 62a arranged in the front-rear direction. One column corresponds to 8 wells 61a and 8 reagent holding portions 62a arranged in the left-right direction. Thus, in the microplate 61 and the reagent container 62, the wells 61a and the reagent holding portions 62a are arranged, respectively, in 12 columns in the front-rear direction and 8 rows in the left-right direction.

Each well 61a of the microplate 61 holds the target DNA molecules and magnetic beads to each of which a plurality of primer molecules for amplifying the target DNA molecule are bound. For example, each well 61a in one row holds the target DNA molecules based on the same subject. For example, each well 61a in one column holds the magnetic beads to each of which the same kind of primer molecules are bound. In this case, by using one microplate 61, it is possible to conduct a test on 8 subjects based on 12 different kinds of primer molecules.

The magnetic beads held in one well 61a include: magnetic beads to each of which a plurality of primer molecules for amplifying a mutated target DNA molecule are bound; and magnetic beads to each of which a plurality of primer molecules for amplifying a normal target DNA molecule are bound. Hereinafter, the mutated target DNA molecule will be referred to as a "variant DNA molecule", and the normal target DNA molecule will be referred to as a "wild-type DNA molecule".

Each reagent holding portion 62a of the reagent container 62 holds a reagent that contains a labeled probe. Each reagent holding portion 62a in one column holds a reagent that contains the same labeled probe. The labeled probe held in one reagent holding portion 62a include: a labeled probe that specifically binds to a variant DNA molecule; and a labeled probe that specifically binds to a wild-type DNA molecule. One reagent container 62 holds reagents respectively having 12 different combinations of labeled probes. The reagent holding portions 62a are respectively associated with the wells 61a of the microplate 61. That is, the labeled probes held in each reagent holding portion 62a in each column label the target DNA molecules in its corresponding well 61a in the same column. Therefore, the transfer unit 30 and the dispensing unit 40 perform dispensing of a reagent containing a combination of labeled probes, with the reagent holding portions 62a respectively associated with the wells 61a that correspond to the reagent holding portions 62a in one-to-one correspondence. That is, the reagent in a reagent holding portion 62a is dispensed into a well 61a at the same position in the front-rear direction and the same position in the left-right direction as the reagent holding portion 62a.

The layout for holding the microplate 61 and the layout for holding the reagent container 62 are not limited to those shown in FIG. 5. It is sufficient that the wells 61a are respectively associated with the reagent holding portions 62a at the same positions in the row direction and the column direction.

Next, the magnet members 80 to be used in a magnetic attraction process will be described.

Figure 6A:
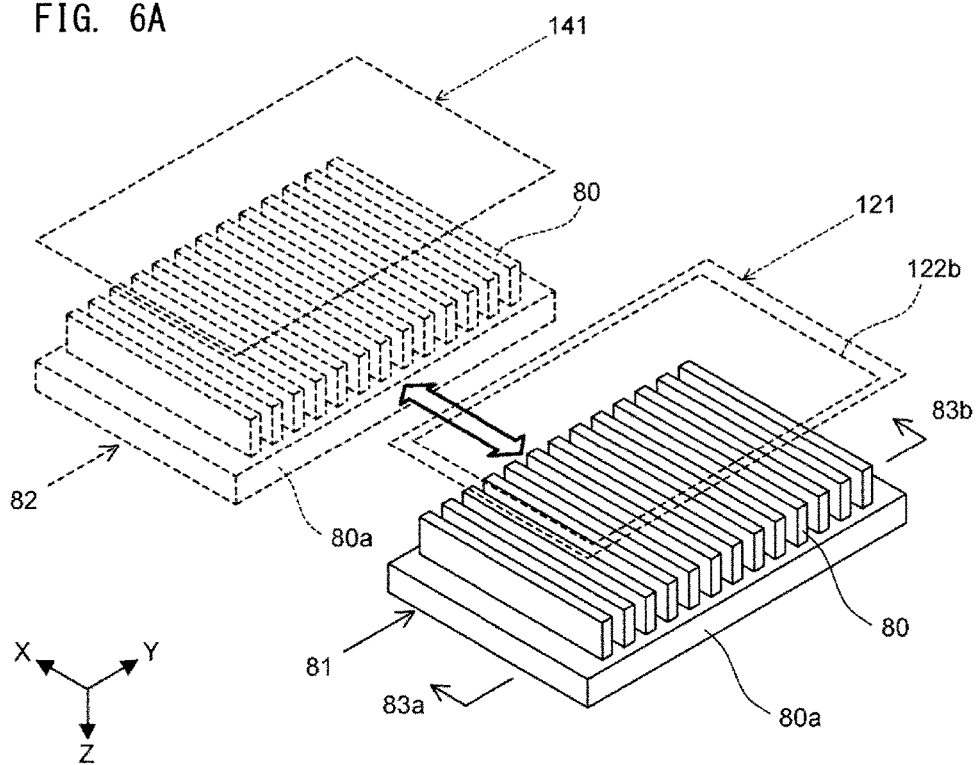
FIG. 6A is a perspective view showing a configuration of a magnet member according to Embodiment 1.

The specimen processing apparatus 10 includes 13 magnet members 80 shown in FIG. 6A, below the bottom surface 20 in the housing 11. Each magnet member 80 is a permanent magnet. The magnet members 80 are supported by a support base 80a which is movable in the X-axis direction. The 13 magnet members 80 each have the same shape, dimensions, and magnetic force. The support base 80a is supported by a support part such as a rail, a shaft, and the like so as to be movable in the X-axis direction. The support base 80a is driven by a drive unit such as a stepping motor, a gear, a belt, and the like. Accordingly, as shown in FIG. 6A, the magnet members 80 are moved between an insertion position 81 which is a position below the microplate placement part 121 and a withdrawn position 82 which is a position below the reagent-container placement part 141. The microplate placement part 121 and the reagent-container placement part 141 are adjacent to each other.

Figure 6B:
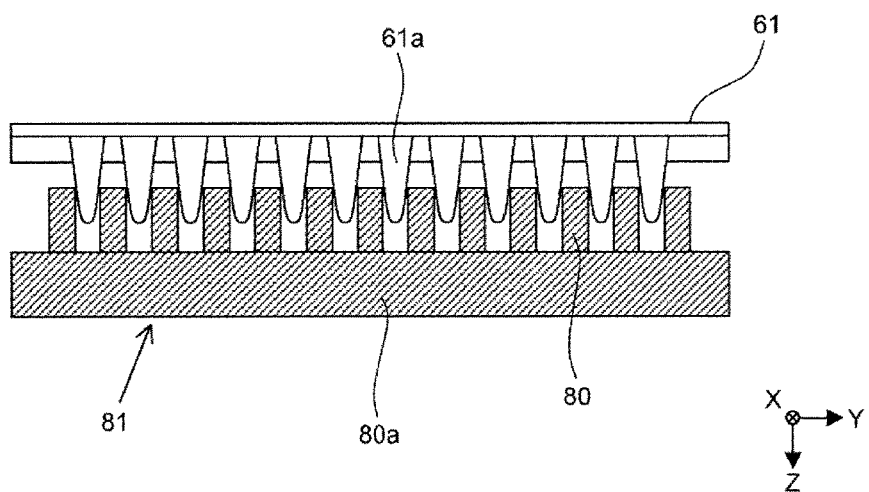
FIG. 6B shows a cross section of the magnet member according to Embodiment 1, viewed from a lateral surface direction.

As shown in FIGS. 6A and 6B, the magnet members 80 are located at the insertion position 81 when the magnetic attraction process is performed. Specifically, as shown in FIG. 6B, the magnet members 80 are respectively inserted between the wells 61a which are on the lower side of the microplate 61 placed in the microplate placement part 121. Accordingly, the magnetic force from the magnet members 80 is applied to the wells 61a from lateral surface directions, and the magnetic beads are attracted to the lateral surfaces in the bottom portions of the wells 61a. In each magnet member 80, the magnetic poles are adjusted so that the magnetic beads can be effectively attracted to the lateral surface in the bottom portion of each well 61a. When the magnetic attraction process is not performed, the magnet members 80 are located at the withdrawn position 82 where the magnet members 80 are withdrawn from the spaces between the wells 61a of the microplate 61.

The magnet members 80 may be withdrawn by moving the magnet members 80 in the Y-axis direction. In this case, nine magnet members 80 that are parallel with each other in the Y-axis direction are provided on the support base 80a. Alternatively, the magnet members 80 may be withdrawn by moving the magnet members 80 in the Z-axis positive direction. However, in the case where the magnet members 80 are withdrawn in the Z-axis positive direction, the size of the apparatus is increased in the Z-axis direction, compared with the cases where the magnet members 80 are withdrawn in the horizontal directions. Thus, desirably, the magnet members 80 are withdrawn in a horizontal direction.

The magnet members 80 may be arranged at positions immediately below the respective wells 61a. In this case, the magnet members 80 may be implemented by an electromagnet which can turn on/off generation of magnetic force. In a case where the magnet members 80 are implemented by an electromagnet, the configuration for moving the magnet members 80 can be omitted. In this case, the magnetic force is applied from immediately below each well 61a. In this manner, when the magnetic force is applied from immediately below each well 61a, the magnetic beads attracted in the magnetic attraction process accumulate on the bottom surface of the well 61a, and accordingly, the magnetic beads could become less likely to be mixed when stirred. In order to avoid this, as shown in FIGS. 6A and 6B, it is desirable to locate the magnet members 80 between the wells 61a.

Next, configurations of the second drive mechanism 42 and the aspiration/discharge unit 43 will be described.

Figure 7:
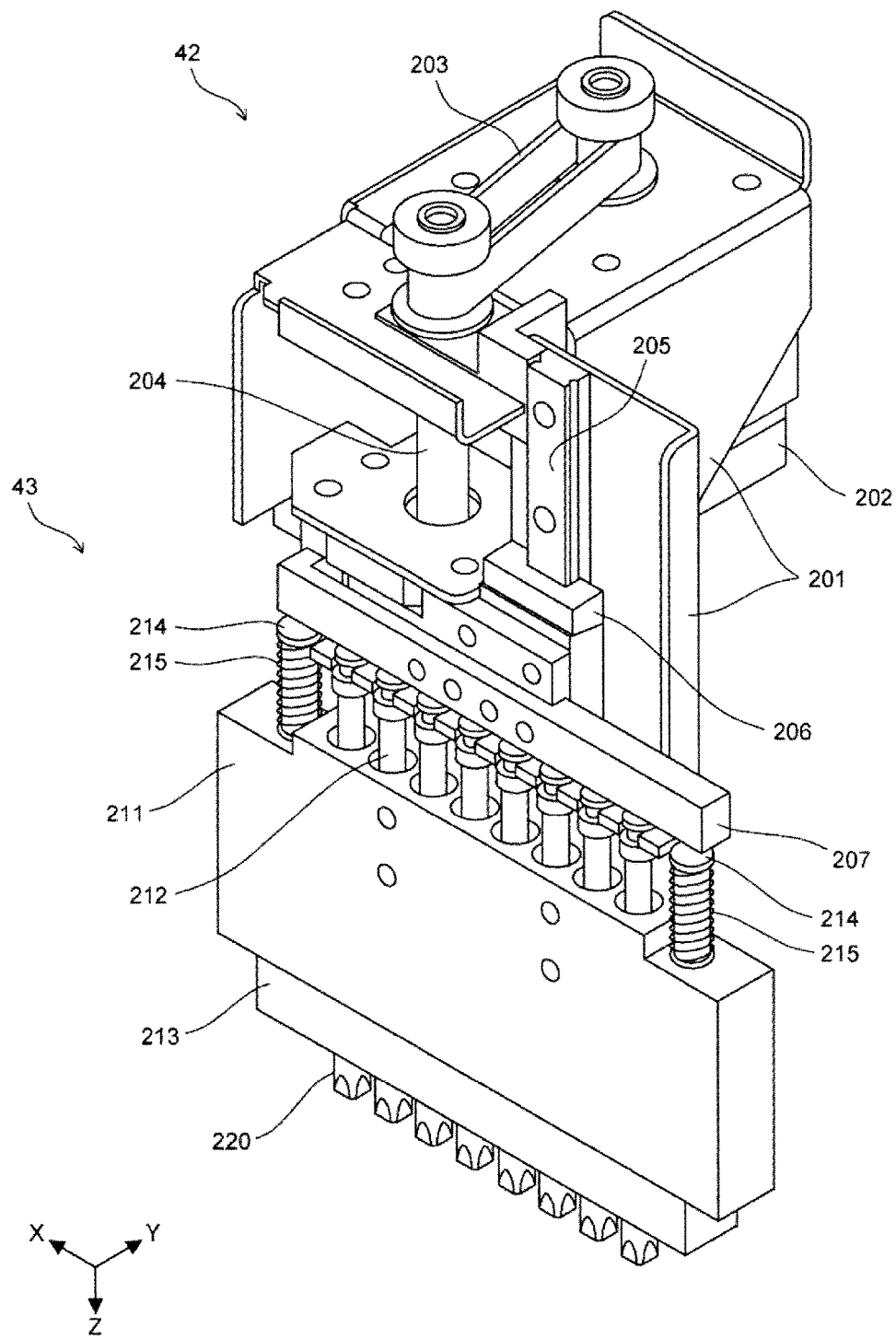
FIG. 7 is a perspective view showing a configuration of a second drive mechanism and an aspiration/discharge unit according to Embodiment 1.

As shown in FIG. 7, the second drive mechanism 42 includes a base member 201, a stepping motor 202, a belt 203, a shaft 204, a rail 205, a sliding part 206, and a raising/lowering bar 207. The aspiration/discharge unit 43 includes a holder 211, eight cylinders 212, a remover 213, two shafts 214, two springs 215, and eight nozzles 220.

The base member 201 is moved in the vertical direction by the first drive mechanism 41 of the dispensing unit 40 shown in FIG. 2. The stepping motor 202 is provided at the base member 201. The belt 203 transmits rotation driving force generated by the stepping motor 202, to the shaft 204. The shaft 204 is rotatably supported by the base member 201. The rail 205 extends in the vertical direction and is provided at the base member 201.

The sliding part 206 is supported by the rail 205 so as to be movable in the up-down direction. On the outer peripheral surface of the shaft 204, a thread groove is formed. The shaft 204 is supported by a ball bearing coupled to the sliding part 206. When the shaft 204 is rotated, the driving force is transmitted to the sliding part 206 via the ball bearing. Accordingly, the sliding part 206 is moved along the rail 205. The raising/lowering bar 207 is provided at the sliding part 206. Thus, by the stepping motor 202 being driven, the raising/lowering bar 207 is moved in the vertical direction.

Figure 8A:
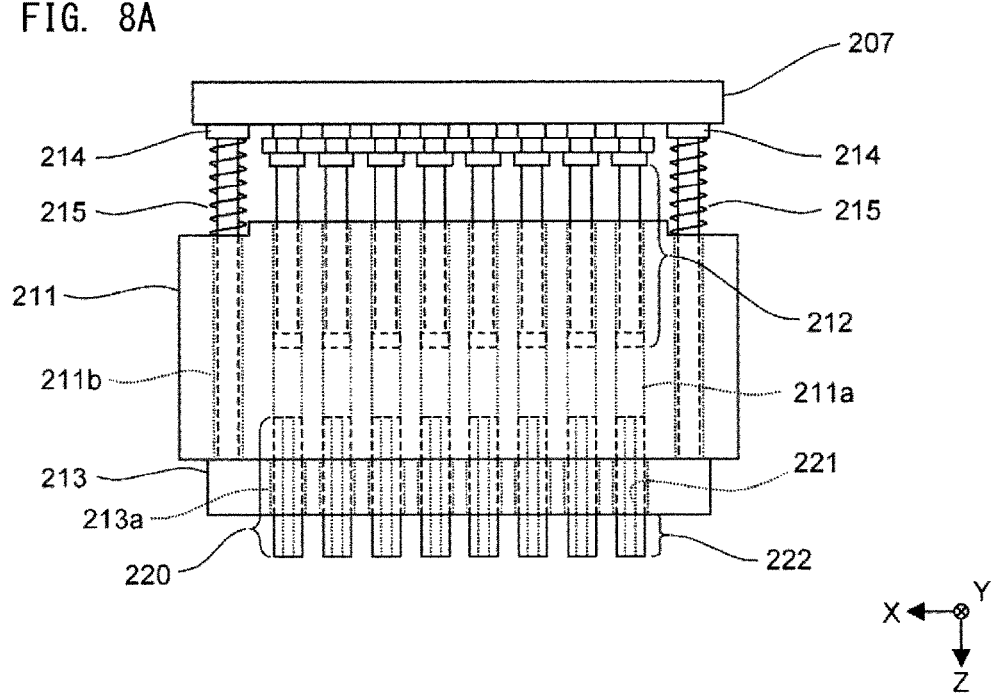
FIG. 8A is a view of a raising/lowering bar and the aspiration/discharge unit according to Embodiment 1, viewed from front.

As shown in FIG. 7 and FIG. 8A, the holder 211 is provided at the base member 201. Eight holes 211a are formed in the holder 211. Two holes 211b are formed such that these eight holes 211a are interposed therebetween. Each of the holes 211a and 211b passes through the holder 211 in the vertical direction. The eight cylinders 212 are respectively inserted into the eight holes 211a from above. The eight nozzles 220 are respectively provided at the lower ends of the eight holes 211a. In each nozzle 220, a hole 221 is formed that passes therethrough in the vertical direction. An end portion 222 near the lower end of the nozzle 220 has a cylindrical shape.

The remover 213 has eight holes 213a formed therein. Each hole 213a passes through the remover 213 in the vertical direction. The eight nozzles 220 are respectively inserted into the eight holes 213a of the remover 213. The two shafts 214 are respectively inserted into the two holes 211b of the holder 211. The lower ends of the two shafts 214 are fixed to the top surface of the remover 213. The springs 215 are connected to the upper ends of the shafts 214, respectively, and to the top surface of the holder 211. The springs 215 apply force upwardly to the shafts 214 in the state shown in FIG. 8A. Under the force from the springs 215, the top surface of the remover 213 is pressed to the lower surface of the holder 211.

Next, operation of the aspiration/discharge unit 43 will be described.

When the apparatus is in the standby state, the raising/lowering bar 207 is located as shown in FIG. 8A relative to the holder 211. At this time, since the shafts 214 are pulled upwardly by the springs 215, the remover 213 enters a state of being in contact with the lower surface of the holder 211. The end portion 222 on the lower side of each nozzle 220 protrudes downwardly by a predetermined length from the lower surface of the remover 213.

Figure 8B:
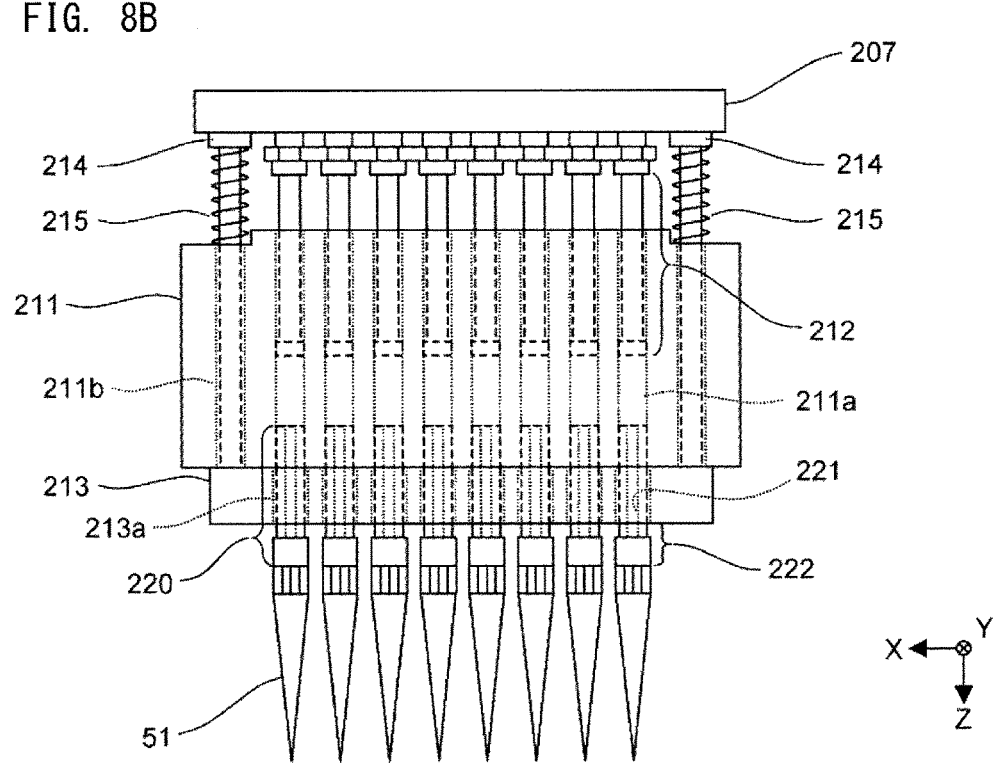
FIG. 8B shows a state in which dispensing tips are attached to nozzles according to Embodiment 1.

In the state shown in FIG. 8A, the dispensing unit 40 is located at the dispensing-tip-container placement part 111 to 117 by the transfer unit 30. Specifically, the eight nozzles 220 are located immediately above eight dispensing tips 51 which are arranged in the X-axis direction and which are rested on the dispensing tip container 50. Subsequently, the second drive mechanism 42 and the aspiration/discharge unit 43 are moved in the Z-axis positive direction by the first drive mechanism 41. Accordingly, all the nozzles 220 are lowered simultaneously, and the end portions 222 of the nozzles 220 are inserted into the openings 51a of the dispensing tips 51. Accordingly, as shown in FIG. 8B, the dispensing tips 51 are respectively attached to the end portions 222 of the nozzles 220. In this manner, since the eight dispensing tips 51 are simultaneously attached to the eight nozzles 220, the time period needed for the attaching can be shortened, compared with a case where the dispensing tips 51 are attached one by one.

Figure 9A:
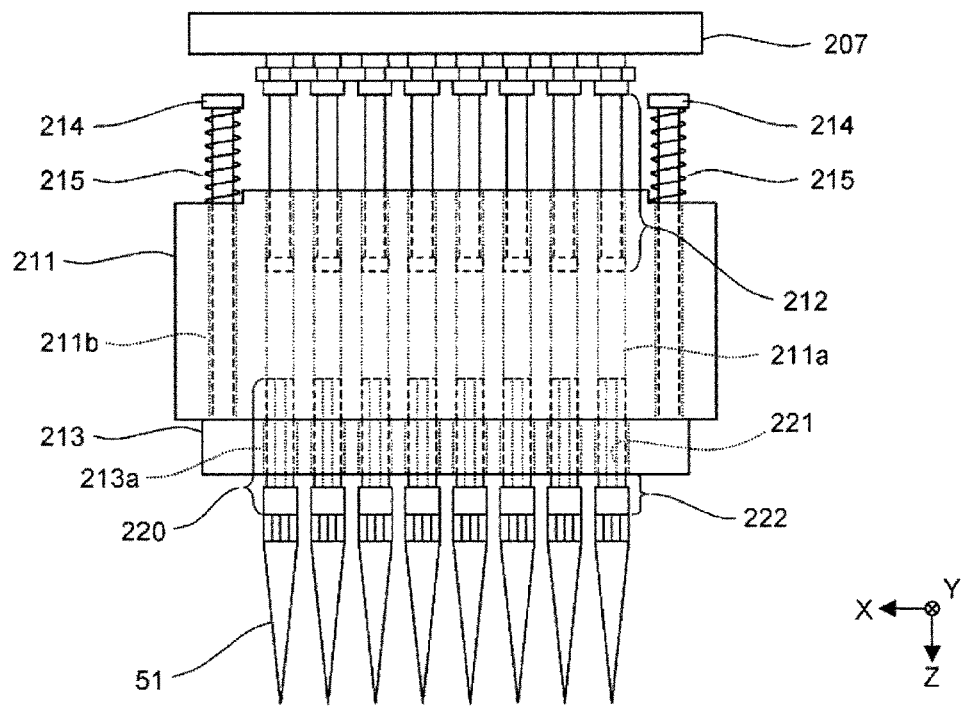
FIG. 9A is a view illustrating that aspiration is performed when the raising/lowering bar according to Embodiment 1 has been raised.

When a liquid is to be aspirated, the dispensing unit 40, with the dispensing tips 51 attached thereto, is transferred by the transfer unit 30 to the corresponding one of the microplate placement part 121, the reagent-container placement parts 131 to 133, and the reagent-container placement part 141. The second drive mechanism 42 and the aspiration/discharge unit 43 are moved downwardly by the first drive mechanism 41. Accordingly, the lower ends 51b of the dispensing tips 51 are moved below the surface of the liquid held in the corresponding one of the microplate 61 and the reagent containers 62, 71. In this state, as shown in FIG. 9A, the raising/lowering bar 207 is moved upwardly by the second drive mechanism 42. Accordingly, the pressure in the holes 211a in the holder 211 is lowered, whereby the liquid is aspirated from the lower ends 51b of the dispensing tips 51.

The aspiration operation is simultaneously performed by the eight dispensing tips 51. That is, in one aspiration operation, the liquid in eight wells 61a arranged in the X-axis direction is aspirated into the eight dispensing tips 51, respectively. In one aspiration operation, the liquid in eight reagent holding portions 62a arranged in the X-axis direction is aspirated into the eight dispensing tips 51, respectively. In one aspiration operation, the liquid in the reagent container 71 placed in the reagent-container placement part 132, 133 is aspirated into the eight dispensing tips 51.

When the aspirated liquid is to be discharged, the raising/lowering bar 207 is moved downwardly by the second drive mechanism 42, to be returned to the original position as shown in FIG. 8B. Accordingly, the aspirated liquid is discharged from the lower ends 51b of the dispensing tips 51.

The discharge operation is simultaneously performed by the eight dispensing tips 51. That is, in one discharge operation, the liquid in the eight dispensing tips 51 is discharged into eight wells 61a arranged in the X-axis direction, respectively. In one discharge operation, the liquid in the eight dispensing tips 51 is discharged into eight reagent holding portions 62a arranged in the X-axis direction, respectively. In one discharge operation, the liquid in the eight dispensing tips 51 is discharged into the reagent container 71 placed in the reagent-container placement part 131.

Figure 9B:
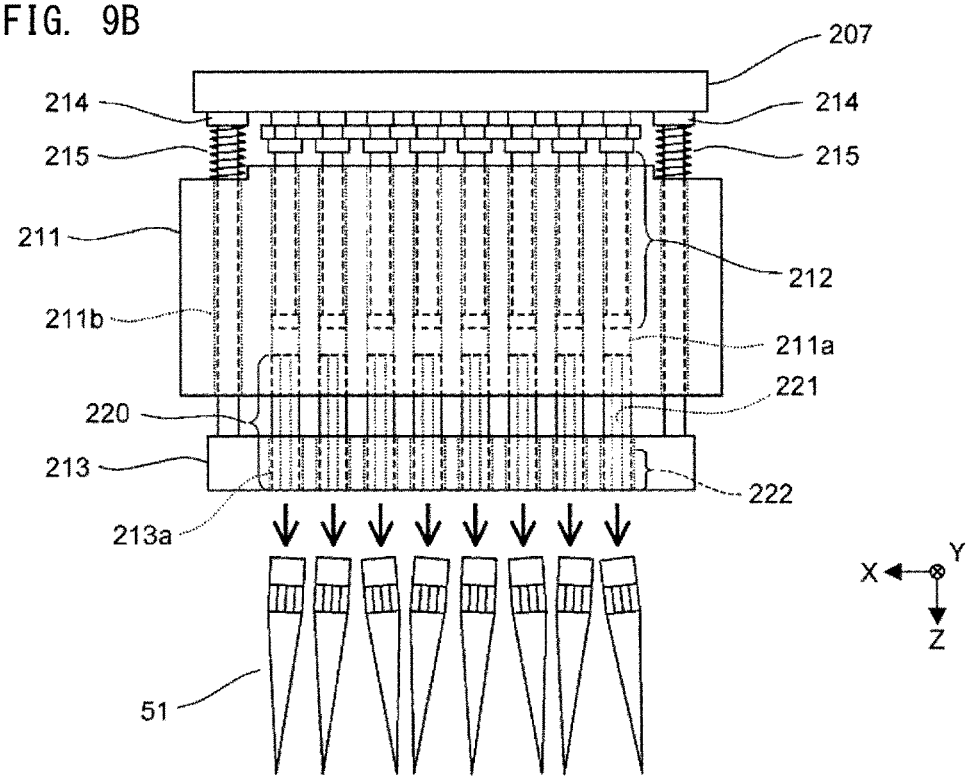
FIG. 9B is a view illustrating that the dispensing tips according to Embodiment 1 are detached from the nozzles.

When the aspiration and the discharge of a liquid have been completed, the dispensing unit 40 is located immediately above the dispensing tip disposal part 13 by the transfer unit 30. Subsequently, from the state shown in FIG. 8B, the raising/lowering bar 207 is moved further downwardly by the second drive mechanism 42. Accordingly, as shown in FIG. 9B, the raising/lowering bar 207 downwardly presses the shafts 214 against the force from the springs 215, whereby the remover 213 is moved downwardly. By the remover 213 being downwardly moved, the dispensing tips 51 attached to the end portions 222 of the nozzles 220 are pressed downwardly by the lower surface of the remover 213. Accordingly, the eight dispensing tips 51 are simultaneously detached from the nozzles 220, to be received in the disposal bag 13a. Then, the raising/lowering bar 207 is moved upwardly by the second drive mechanism 42, to be returned to the original positions as shown in FIG. 8A.

Next, the shape of the end portion 222 of the nozzle 220 will be described.

As shown in FIG. 1 OA, an inner lateral surface 51c near the upper end of the dispensing tip 51 has a shape whose diameter is gradually reduced downwardly. The horizontal cross section of the inner lateral surface 51c is substantially circular. Thus, a nozzle 220 of Comparative Example 1 shown in FIG. 10A is conceivable. In Comparative Example 1, the end portion 222 of the nozzle 220 has a substantially cylindrical shape, but strictly speaking, has a shape whose diameter is gradually reduced downwardly as in the case of the inner lateral surface 51c of the dispensing tip 51. The horizontal cross section of the end portion 222 of the nozzle 220 is substantially circular. The end portion 222 of Comparative Example 1 fits in close contact with the inner lateral surface 51c of the dispensing tip 51.

In the case of Comparative Example 1, if the dispensing tip 51 is appropriately attached as shown in FIG. 1 OA, the dispensing tip 51 does not tilt after being attached. However, it could happen that the dispensing tip 51 is held in a dispensing tip container 50, in a state where the dispensing tip 51 is slightly shifted in the horizontal direction from the normal position. In such a case, with the configuration of Comparative Example 1, as shown in FIG. 10B, even if each dispensing tip 51 is rested on the dispensing tip container 50 vertically, it could happen that the tip of the nozzle 220 abuts against the upper end of the dispensing tip 51 when the nozzle 220 is lowered, whereby the dispensing tip 51 cannot be appropriately attached to the nozzle 220.

Thus, a nozzle 220 of Comparative Example 2 shown in FIG. 10C is conceivable. The nozzle 220 of Comparative Example 2 is configured such that the lateral surface of the end portion 222 of the nozzle 220 of Comparative Example 1 is cut out along the entire circumference thereof. This allows the lateral surface of the end portion 222 to extend to be further closer to the center of the nozzle 220 toward the tip of the nozzle 220. Accordingly, in the case of Comparative Example 2, the tip of the nozzle 220 is less likely to abut against the upper end of the dispensing tip 51 when the nozzle 220 is lowered. Therefore, even if the dispensing tip 51 is held in the dispensing tip container 50 in a state where the dispensing tip 51 is slightly shifted in the horizontal direction, the dispensing tip 51 can be appropriately attached to the end portion 222 of the nozzle 220 as shown in FIG. 10C.

However, in the case of Comparative Example 2, at the time of attaching the dispensing tip 51, when the nozzle 220 is lowered and the dispensing tip 51 rested on the dispensing tip container 50 is downwardly pressed by the nozzle 220, there are cases where a placement surface 50a on which the dispensing tip 51 is rested flexes under the load from the nozzle 220, thereby causing the dispensing tip 51 to be tilted, as shown in FIG. 10D. In this case, in Comparative Example 2, since the tip portion of the nozzle 220 is cut out along the entire circumference thereof, the diameter of the tip portion of the nozzle 220 is smaller than the diameter of the dispensing tip 51. Therefore, as shown in FIG. 10E, the dispensing tip 51 is attached to the end portion 222 in a state where the dispensing tip 51 is slightly tilted relative to the vertical direction. If the dispensing tip 51 is attached in such a tilted state, the aspiration and the discharge cannot be appropriately performed with respect to the well 61a of the microplate 61 and the reagent holding portion 62a of the reagent container 62.

Figure 11A:
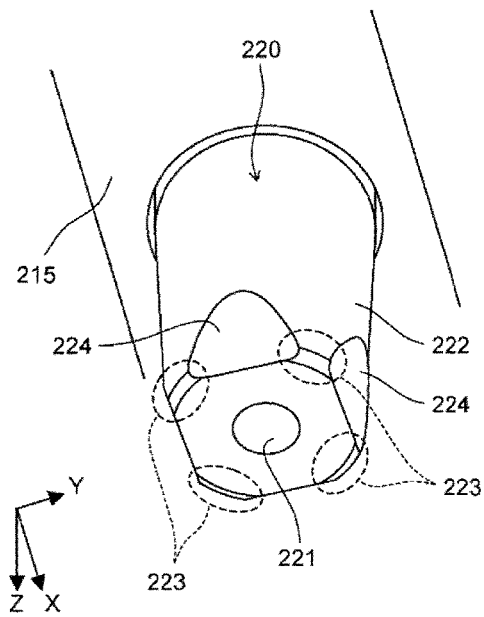
FIG. 11A is a perspective view showing a configuration of a nozzle according to Embodiment 1.
Figure 11B:
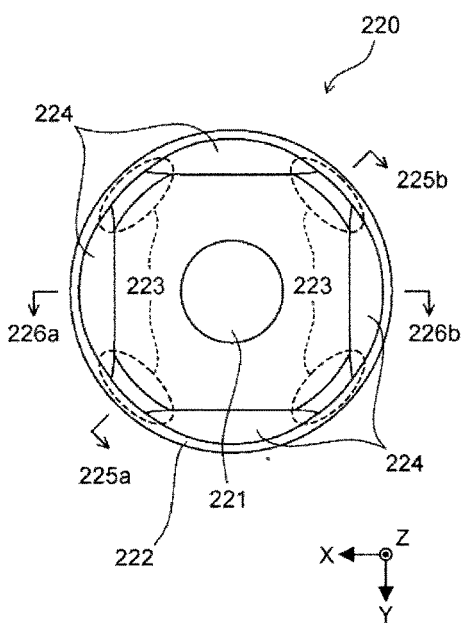
FIG. 11B is a view of the nozzle according to Embodiment 1, viewed from below.

Thus, in Embodiment 1, as shown in FIGS. 11A and 11B, the lateral surface of the end portion 222 of the nozzle 220 is partially cut out so as to extend to be closer to the center of the nozzle 220 toward the tip of the nozzle 220. That is, the nozzle 220 according to Embodiment 1 is configured such that the lateral surface of the end portion 222 of the nozzle 220 of Comparative Example 1 is partially cut out, instead of being cut out along the entire circumference as in Comparative Example 2.

Specifically, in the end portion 222 of the nozzle 220, four lateral surface portions 223, extending along a circle having a diameter substantially identical to that of the inner lateral surface 51c, are left in the circumferential direction of the fitted portion of the dispensing tip 51. Between adjacent lateral surface portions 223, an inclined surface 224 extending so as to be closer to the center of the nozzle 220 toward the tip of the nozzle 220 is formed. The four inclined surfaces 224 are respectively formed at the front, rear, left, and right positions of the end portion 222.

When the dispensing tip 51 has been attached to the nozzle 220 according to Embodiment 1, if a cross section 225a-225b shown in FIG. 11B is viewed from the lateral surface direction, the cross section is the same as that shown in FIG. 10A. If a cross section 226a-226b shown in FIG. 11B is viewed from the lateral surface direction, the cross section is the same as that shown in FIG. 10C. Thus, when the end portion 222 of the nozzle 220 is fitted into the dispensing tip 51, as in the case shown in FIG. 10A, the four lateral surface portions 223 come into contact with the inner lateral surface 51c of the dispensing tip 51, whereby the dispensing tip 51 is supported by the end portion 222 without being tilted. In addition, as in the case shown in FIG. 10C, since the four inclined surfaces 224 do not come into contact with the inner lateral surface 51c of the dispensing tip 51, even if the position of the dispensing tip 51 has been slightly shifted, the end portion 222 is inserted into the dispensing tip 51.

Figure 11C:
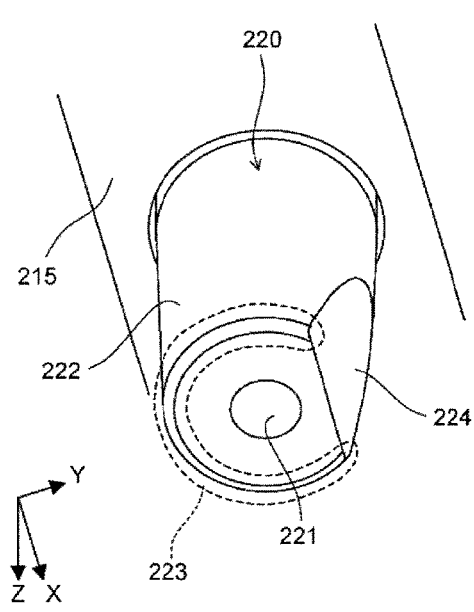
FIG. 11C is a perspective view showing a configuration of a nozzle according to Modification.
Figure 11D:
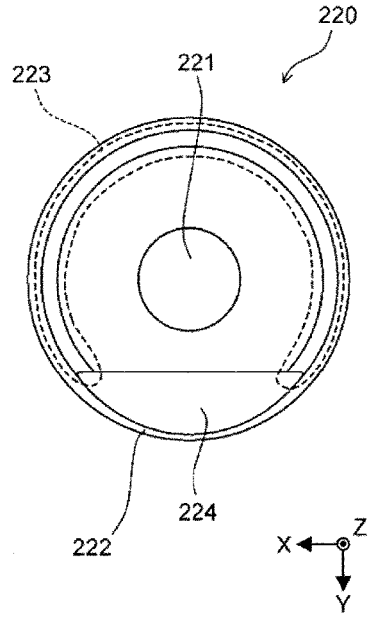
FIG. 11D is a view of the nozzle according to Modification, viewed from below.

As shown in FIGS. 11C and 11D, in the end portion 222, only one inclined surface 224 may be formed and one lateral surface portion 223 may be formed. Also in this case, thanks to the lateral surface portion 223, the dispensing tip 51 is supported by the end portion 222 without being tilted, and thanks to the inclined surface 224, the end portion 222 is inserted into the dispensing tip 51 even if the position of the dispensing tip 51 has been slightly shifted. Other than this, two, three, or five lateral surface portions 223 may be left in the end portion 222, and the lateral surface portions 223 may be at positions shifted from the front, rear, left, and right positions in the circumferential direction. It is sufficient that the lateral surface portions 223 can support the dispensing tip 51 in an appropriate attitude, by coming into contact with the inner lateral surface 51c of the dispensing tip 51. The lateral surface portions 223 may not necessarily be left in arc shapes along the circumferential direction as shown in FIGS. 11A and 11B, and may be left in dot shapes along the circumferential direction.

Figure 12:
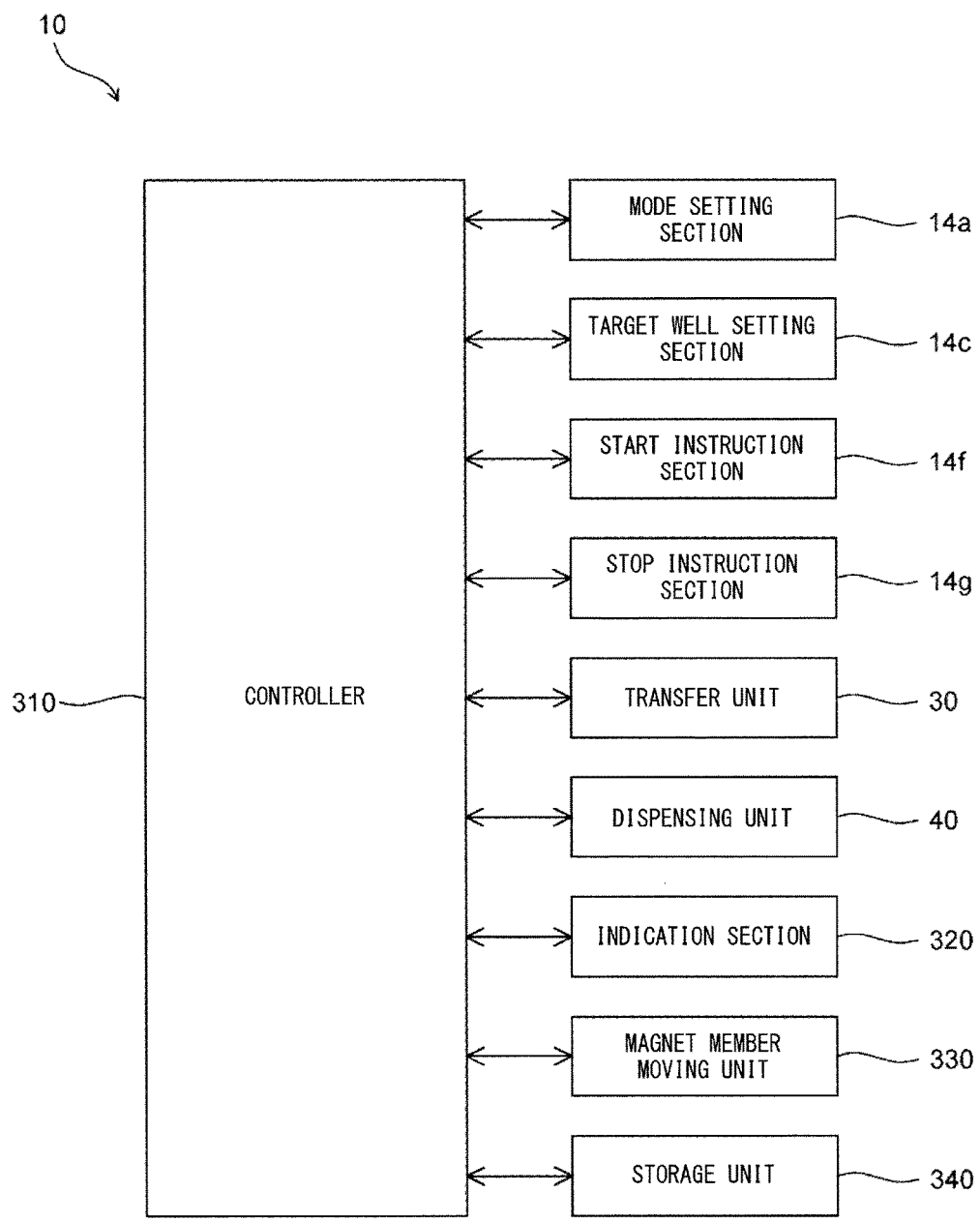
FIG. 12 is a block diagram showing a configuration of the specimen processing apparatus for genetic testing according to Embodiment 1.

As shown in FIG. 12, the specimen processing apparatus 10 includes the mode setting section 14a, the target well setting section 14c, the start instruction section 14f, the stop instruction section 14g, the transfer unit 30, the dispensing unit 40, a controller 310, an indication section 320, a magnet member moving unit 330, and a storage unit 340. The controller 310 is implemented by a CPU. The controller 310 receives signals from components of the specimen processing apparatus 10, and controls the components. The storage unit 340 is composed of a RAM, a ROM, a hard disk, and the like.

The indication section 320 includes the light-emitters 111a to 117a, 121a, 131a, 132a to 132c, 133a, and 141a. The indication section 320 may not include these light-emitters but may be implemented by a display unit. In this case, for example, the layout of the inside of the housing 11 as shown in FIG. 2 is displayed on the display unit, and instead of the light-emitters being lit, corresponding positions on the layout are indicated red. The magnet member moving unit 330 includes: a support part which supports the support base 80a in FIGS. 6A and 6B in such a manner as to be movable in the X-axis direction; and a drive unit for driving the support base 80a.

Next, with reference to FIG. 13, a flow of genetic testing according to the BEAMing method that uses the specimen processing apparatus 10 will be described. In Embodiment 1, a thermal cycler and a flow cytometer are used, separately from the specimen processing apparatus 10.

The operator performs a preparatory process by hand, first. Specifically, the operator extracts DNA from a blood specimen of a subject to perform PCR amplification, and dilutes the specimen containing the amplified DNA, to an extent that allows the emulsion preparation process to be performed. Then, as shown in (a) of FIG. 14, into wells 61a of the microplate 61, the operator puts the specimen containing the amplified DNA, and magnetic beads to each of which a plurality of primer molecules are bound.

In step S11, the operator sets the microplate 61 prepared as above, to the specimen processing apparatus 10, and performs the emulsion preparation process described later. In the emulsion preparation process, the emulsion reagent is dispensed into the wells 61a. Accordingly, in each well 61a, an oil phase is formed in an aqueous phase that contains magnetic beads to each of which a plurality of primer molecules for amplifying the target DNA molecule are bound, whereby a water-in-oil type (W/O type) emulsion to be subjected to PCR is prepared. As shown in (b) of FIG. 14, in the liquid in the well 61a, a large number of droplets each containing about one magnetic bead and one target DNA molecule are prepared.

In step S21, the operator sets, to the thermal cycler, the microplate 61 having been subjected to the emulsion preparation process, and performs the PCR process. The thermal cycler performs a process of repeating, a plurality of times, one cycle in which the temperature of the microplate 61 is changed to a plurality of different temperatures. As a result, in each droplet of the W/O type emulsion prepared in the emulsion preparation process, the target DNA molecule is amplified. As shown in (c) of FIG. 14, the target DNA molecule is amplified inside the droplet.

In step S12, the operator sets again, to the specimen processing apparatus 10, the microplate 61 having been subjected to the PCR process, and performs the emulsion breaking process described later. In the emulsion breaking process, the first breaking reagent and the second breaking reagent are dispensed into the well 61a. Accordingly, the W/O type emulsion having been subjected to PCR are broken in the well 61a, and magnetic beads are collected from the droplets. In the emulsion breaking process, after the first breaking reagent and the second breaking reagent have been dispensed, the reagent containing the labeled probes is dispensed into the well 61a. Accordingly, the labeled probes can be hybridized to the amplified target DNA molecules.

In step S22, the operator sets again, to the thermal cycler, the microplate 61 having been subjected to the emulsion breaking process, and performs the hybridization process. The thermal cycler performs the process of changing the temperature of the microplate 61 to a plurality of different temperatures. As a result, as shown in (d) of FIG. 14, the variant DNA molecules and the wild-type DNA molecules in the well 61a are bound to their corresponding labeled probes, whereby the variant DNA molecules and the wild-type DNA molecules are labeled with fluorescence.

In step S13, the operator sets again, to the specimen processing apparatus 10, the microplate 61 having been subjected to the hybridization process, and performs the washing process described later. In the washing process, the PBS as a washing reagent is dispensed into the well 61a. Through the washing process, BF separation is performed in the well 61a, and labeled probes that remain unreacted are aspirated to be separated from the magnetic beads. In other words, leaving magnetic beads to which the target DNA molecules and the labeled probes are bound, the labeled probes that are not bound to magnetic beads are removed. In addition, the solvent is replaced with the PBS.

In step S31, the operator sets, to the flow cytometer, the microplate 61 having been subjected to the washing process, and performs the measurement process. Accordingly, the magnetic beads washed in the washing process are measured in the flow cytometer, the number of magnetic beads to which the labeled probes are bound is counted.

Specifically, for each well 61a, the flow cytometer aspirates a measurement sample in the well 61a, causes the measurement sample to flow in a flow cell, and irradiates the measurement sample flowing in the flow cell, with laser light from a laser light source. At this time, fluorescence is generated from the labeled probe bound to each variant DNA molecule and the labeled probe bound to each wild-type DNA molecule. The flow cytometer separates, by means of a dichroic mirror, the two kinds of fluorescence which have been generated from the labeled probes and which have different wavelengths. Then, the flow cytometer detects these two kinds of fluorescence by means of different detectors. On the basis of output signals from the respective detectors, the flow cytometer counts the number of magnetic beads to which the variant DNA molecules in the measurement sample are bound, and the number of magnetic beads to which the wild-type DNA molecules in the measurement sample are bound. It should be noted that the flow cytometer may further include another detector in order to detect forward scattered light generated from each magnetic bead in the measurement sample.

For each well 61a, the operator obtains the ratio of the number of magnetic beads to which the variant DNA molecules are bound, relative to the total of the number of magnetic beads to which the variant DNA molecules are bound and the number of magnetic beads to which the wild-type DNA molecules are bound. In this manner, the operator can know the mutation state of the target DNA molecules with respect to the subject from whom the target DNA molecules have been obtained. It should be noted that the ratio of the number of magnetic beads to which the variant DNA molecules are bound, relative to the number of magnetic beads to which the wild-type DNA molecules are bound, may be obtained.

Next, a specific process performed by the specimen processing apparatus 10 will be described with reference to flow charts.

Figure 15B:
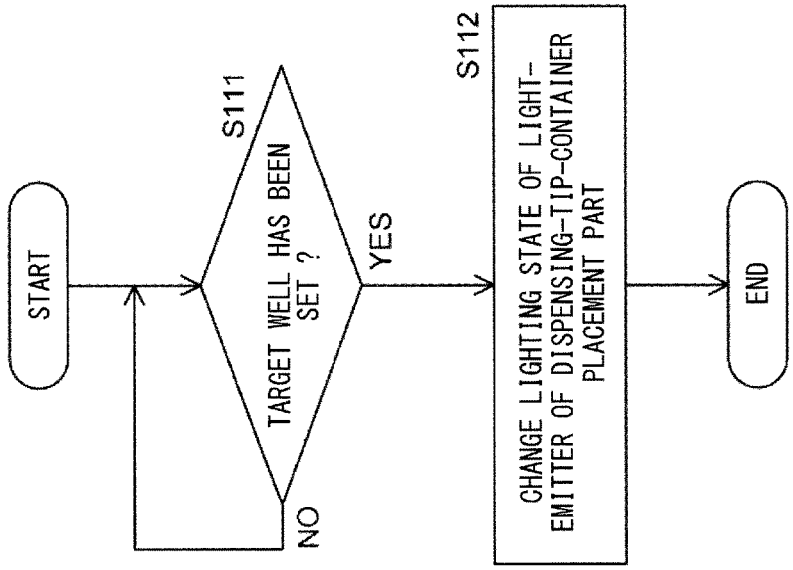
FIG. 15B is a flow chart according to Embodiment 1, showing a process performed when the number of wells to be processed is set.
Figure 15A:
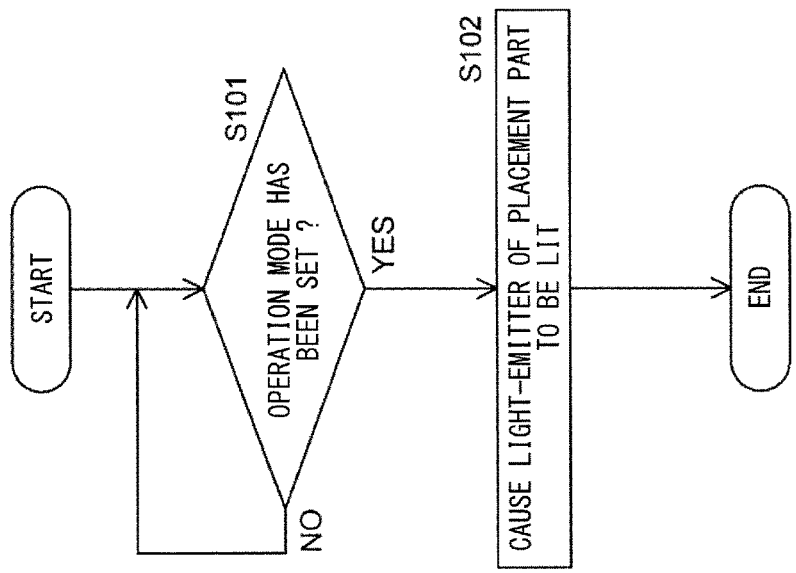
FIG. 15A is a flow chart according to Embodiment 1, showing a process performed when an operation mode is set.

As shown in FIG. 15A, in step S101, the controller 310 determines whether the operation mode has been set via the mode setting section 14a by the operator. When the operation mode has been set, the controller 310 causes, in step S102, the light-emitters of the dispensing-tip-container placement parts 111 to 117 to be lit, in accordance with the set operation mode and the number of columns of the wells 61a to be processed. It should be noted that, immediately after the power supply of the specimen processing apparatus 10 has been turned on, the operation mode is set to the emulsion preparation mode as the initial setting, the number of columns to be processed is set to 12, and the process of step S102 is performed in accordance with the initial setting. The process shown in FIG. 15A is repeated in the standby state.

The light-emitters to be lit in step S102 are as shown in FIG. 16. In FIG. 16, 14 light-emitters are shown in the vertical direction, and the operation modes and the number of columns to be processed are shown in the horizontal direction. A circle indicates that a light-emitter is to be lit. When the operation mode is the emulsion preparation mode, irrespective of the number of columns to be processed, only the light-emitters 111a, 121a, 131a, and 132a are lit. When the operation mode is the emulsion breaking mode, the light-emitters 111a to 117a are lit in accordance with the number of columns to be processed. In addition to this, when the operation mode is the emulsion breaking mode, irrespective of the number of columns to be processed, the light-emitters 121a, 131a, 132b, 133a, and 141a are lit. When the operation mode is the wash mode, the light-emitters 111a to 117a are lit in accordance with the number of columns to be processed. In addition, when the operation mode is the wash mode, the light-emitters 121a, 131a, and 132c are lit.

The storage unit 340 shown in FIG. 12 retains the table shown in FIG. 16 in advance. On the basis of this table, the controller 310 controls the light-emitters 111a to 141a.

As described above, when the operation mode is set, the light-emitters of the placement parts into which containers need to be placed are lit, whereby the operator is urged to place the containers therein. Accordingly, the operator can place the exact number of containers by confirming the light-emitters. Meanwhile, the number of dispensing tips 51 to be used changes depending on the operation mode and the number of columns to be processed, and associated with the number of dispensing tips 51 to be used, the number of dispensing tip containers 50 that need to be placed also changes. However, since the light-emitters of the dispensing-tip-container placement parts 111 to 117 are lit in accordance with the number of dispensing tip container 50 that need to be placed, the operator can place the exact number of dispensing tip containers 50. For confirming a light-emitter so as to place a container, a label indicating the kind of the container that should be placed in the placement part is provided at a position adjacent the light-emitter. Accordingly, the operator can grasp the kind of the container that should be placed.

As shown in FIG. 15B, in step S111, the controller 310 determines whether the number of columns of the wells 61a to be processed has been set via the target well setting section 14c by the operator. When the number of columns to be processed has been set, the controller 310 changes, in step S112, the lighting state of the light-emitters of the dispensing-tip-container placement parts 111 to 117 in accordance with the operation mode and the set number of columns to be processed. Also in this case, lighting of the light-emitters 111a to 117a is performed as shown in FIG. 16. The process shown in FIG. 15B is repeated in the standby state.

As described above, when the number of wells 61a to be processed has been set, the number of dispensing-tip-container placement parts into which the dispensing tip containers 50 need to be placed changes, and the lighting state of the light-emitters is changed. Accordingly, the operator can place the exact number of dispensing tip containers 50 by confirming the light-emitters.

The operator sets the operation mode and the number of columns to be processed, and then, sets containers and the like which need to be placed, while confirming the light-emitters. Then, the operator presses the start instruction section 14f to execute the targeted process.

Figure 17:
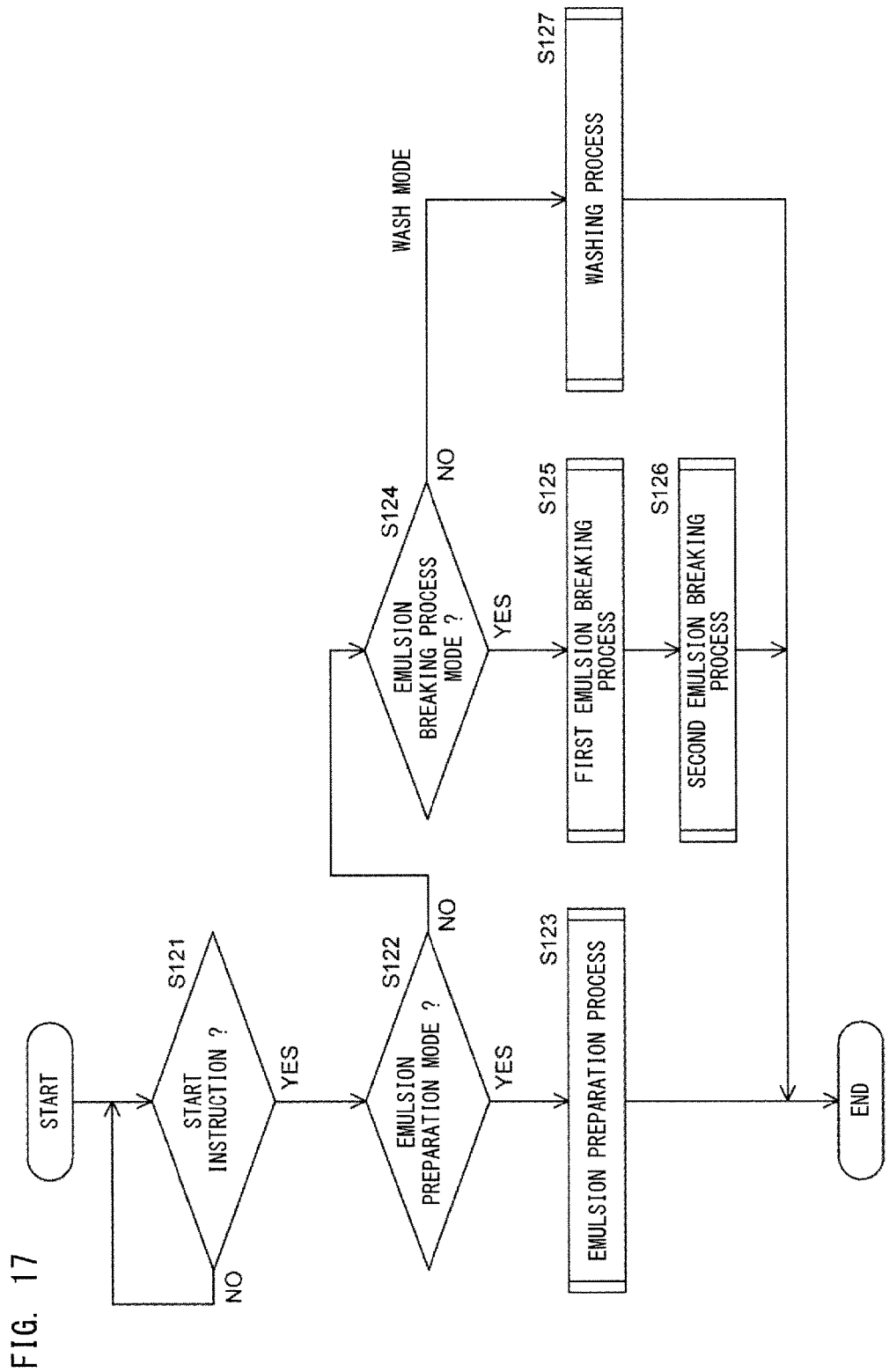
FIG. 17 is a flow chart showing a process according to Embodiment 1, performed when a start instruction has been made.

As shown in FIG. 17, in step S121, the controller 310 determines whether a start instruction has been made via the start instruction section 14f by the operator. When the start instruction has been made, the controller 310 determines the set operation mode, and starts a process in accordance with the operation mode.

When the operation mode is the emulsion preparation mode, the controller 310 performs the emulsion preparation process in step S123. When the operation mode is the emulsion breaking mode, the controller 310 performs a first emulsion breaking process in step S125, and performs a second emulsion breaking process in step S126. The emulsion breaking process includes the first emulsion breaking process and the second emulsion breaking process. When the operation mode is the wash mode, the controller 310 performs the washing process in step S127. When the process of steps S123, S126, or S127 has ended, the specimen processing apparatus 10 enters the standby state, and the process is returned to step S121.

Thus, when performing the emulsion preparation process, the emulsion breaking process, and the washing process, the operator only has to make settings via the mode setting section 14*a* and the target well setting section 14*c*, place necessary containers and the like, and then press the start instruction section 14*f*. Accordingly, the above-described processes can be automatically performed through simple operations, and thus, the burden on the laboratory technician can be reduced, and the specimen pretreatment for genetic testing which uses the emulsion can be made efficient.

Next, the emulsion preparation process, the first and second emulsion breaking processes, and the washing process will be described in order, with reference to flow charts.

In the processes below, attachment and detachment of the dispensing tips 51, aspiration and discharge by the dispensing tips 51, and movement in the horizontal direction and the vertical direction of the nozzles 220 are performed, by the controller 310 driving the transfer unit 30 and the dispensing unit 40. Attachment of the dispensing tips 51 is sequentially performed with respect to the dispensing tip containers 50 placed in the dispensing-tip-container placement parts 111 to 117. In one dispensing tip container 50, the attachment is sequentially performed from the rear column toward the front column. The magnet members 80 are assumed to be at the withdrawn position 82, unless otherwise specified.

Figure 18:
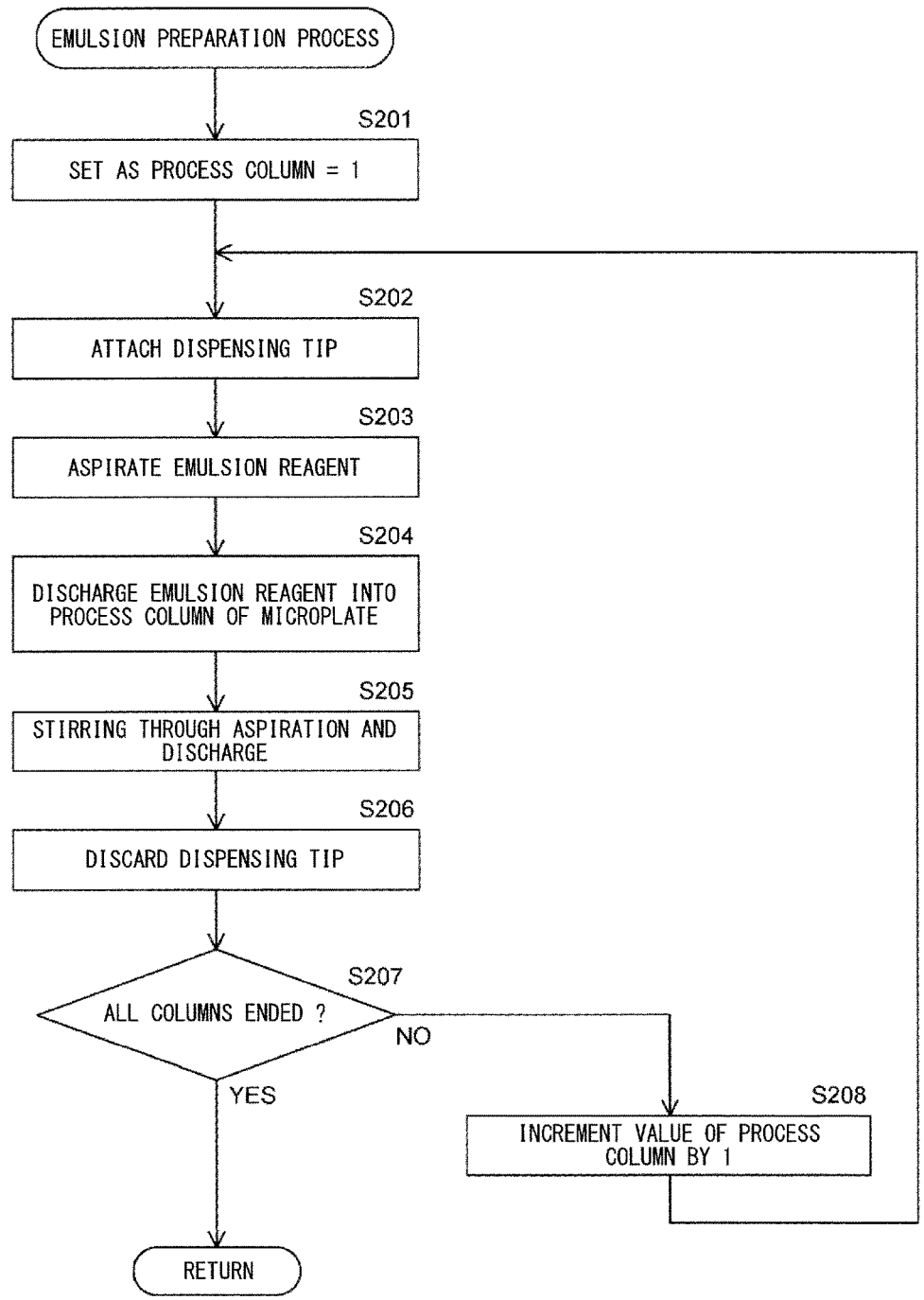
FIG. 18 is a flow chart showing an emulsion preparation process according to Embodiment 1.

With reference to FIG. 18, the emulsion preparation process will be described.

In step S201, the controller 310 sets 1 for the process column, thereby setting the process column to the rearmost column of the microplate 61. By the value of the process column being incremented by 1 in step S208 described later, the process column is sequentially shifted forward by one by one. The value of the process column is stored in the storage unit 340. In step S202, as described with reference to FIG. 8A, the controller 310 causes dispensing tips 51 to be attached to the eight nozzles 220, respectively. In step S203, the controller 310 causes the emulsion reagent in the reagent container 71 placed in the reagent-container placement part 131, to be aspirated. In step S204, the controller 310 causes the emulsion reagent to be discharged into the process column of the microplate 61. In step S205, the controller 310 causes the liquid in each well 61*a* to be stirred through aspiration and discharge thereof.

Here, with reference to (a) to (h) of FIG. 19, the stirring through aspiration and discharge will be described. (a) to (h) of FIG. 19 each show the dispensing tip 51 and the well 61*a* viewed in the X-axis positive direction. The Y-axis positive direction corresponds to the rearward direction, and the Y-axis negative direction corresponds to the forward direction.

Figure 19:
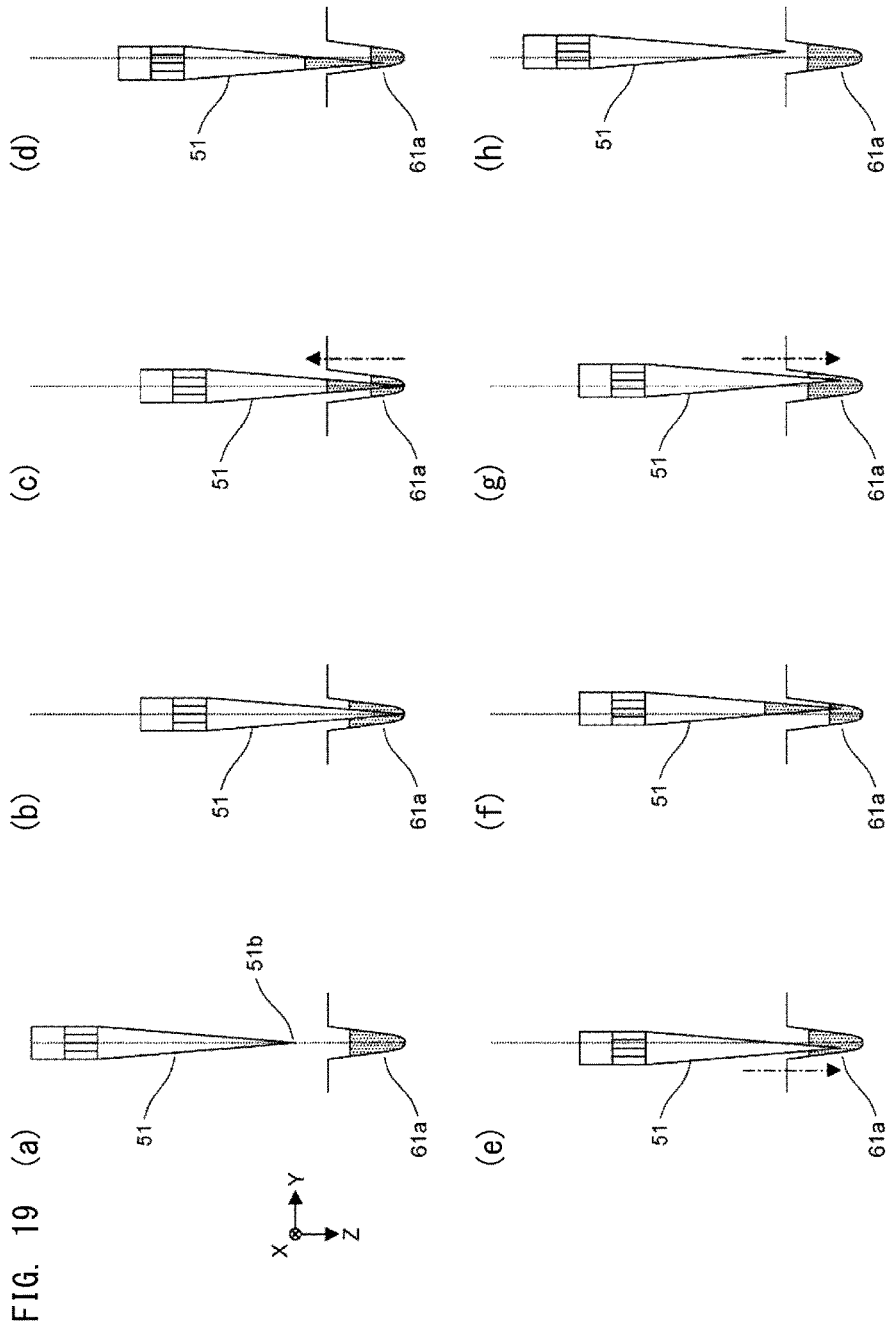
FIG. 19 shows movement of the dispensing tip in stirring through aspiration and discharge and timings of aspiration and discharge according to Embodiment 1.

As shown in (a) of FIG. 19, first, the dispensing tip 51 is located immediately above the well 61*a*, and the central axis of the dispensing tip 51 is aligned with the central axis of the well 61*a*. As shown in (b) of FIG. 19, the dispensing tip 51 is lowered, and as shown in (c) of FIG. 19, the liquid in the well 61*a* is aspirated. Subsequently, the dispensing tip 51 is raised in such a manner as to prevent the lower end 51*b* of the dispensing tip 51 from coming above the liquid surface, and then, as shown in (d) of FIG. 19, the dispensing tip 51 is moved forward such that the central axis of the dispensing tip 51 is located slightly forward relative to the central axis of the well 61*a*. Then, as shown in (e) of FIG. 19, the liquid is discharged.

Subsequently, the dispensing tip 51 is moved rearward such that the central axis of the dispensing tip 51 is aligned with the central axis of the well 61*a*, and then, as shown in (b) of FIG. 19, the dispensing tip 51 is lowered. Then, as shown in (c) of FIG. 19, the liquid in the well 61*a* is aspirated. Subsequently, the dispensing tip 51 is raised in such a manner as to prevent the lower end 51*b* of the dispensing tip 51 from coming above the liquid surface, and then, as shown in (f) of FIG. 19, the dispensing tip 51 is moved rearward such that the central axis of the dispensing tip 51 is located slightly rearward relative to the central axis of the well 61*a*. Then, as shown in (g) of FIG. 19, the liquid is discharged.

Subsequently, the dispensing tip 51 is moved forward such that the central axis of the dispensing tip 51 is aligned with the central axis of the well 61*a*, and then, the dispensing tip 51 is lowered as shown in (b) of FIG. 19. In the stirring through aspiration and discharge, the stirring steps as shown in (b) to (g) of FIG. 19 are repeated a plurality of times. When the stirring through aspiration and discharge has ended, the dispensing tip 51 is raised from the position where the discharge has been performed last, as shown in (h) of FIG. 19.

In this manner, when the steps of stirring the liquid in the well 61*a* through aspiration and discharge thereof are performed, the discharge is performed at a different position near the lateral surface of the well 61*a* in each step. Specifically, the discharge is repeatedly performed at the two front and rear positions between which the center of the well 61*a* is located. Here, there are cases where the position of the dispensing tip 51 is slightly shifted relative to the nozzle 220 within an allowable range. In such a case, if the discharge is performed at only one position, there are cases where effective stirring cannot be realized depending on the positional shift of the dispensing tip 51. However, in Embodiment 1, even if the discharge at either the front position or the rear position cannot realize effective stirring, since the discharge at the front position and the discharge at the rear position are alternately repeated, and thus, effective stirring can be sufficiently realized.

In the stirring through aspiration and discharge that is performed after the magnetic attraction process described later, it is desirable in particular that the discharge is repeatedly performed at the two front and rear positions between which the center of the well 61*a* is located as described above. That is, when the magnetic attraction process is performed, magnetic beads are attracted to the lateral surface of the well 61*a*, but if the discharge is performed as described above, the magnetic beads attracted to the lateral surface of the well 61*a* can be effectively removed from the lateral surface. Thus, if the discharge is repeatedly performed at the front and rear positions, then, in the stirring through aspiration and discharge that is performed after the magnetic attraction process, the liquid in the well 61*a* can be especially effectively stirred.

In addition, since the aspiration is performed in a state where the central axis of the dispensing tip 51 is aligned with the central axis of the well 61*a*, the lower end 51*b* of the dispensing tip 51 can be located at the lowest part of the well 61*a*, for example. Accordingly, even in a case where sediment of components is present in the lowest part, the liquid in the well 61*a* can be effectively stirred. In the stirring through aspiration and discharge, the aspiration of the liquid may be performed at a position where the central axis of the dispensing tip 51 is shifted in the front-rear direction relative to the central axis of the well 61*a*. However, in such a case, since the lower end 51*b* cannot be located at the lowest part, it is desirable that the aspiration of the liquid is performed in a state where the central axis of the dispensing tip 51 is aligned with the central axis of the well 61*a* as described above.

As described above, the stirring through aspiration and discharge in step S204 is performed in a state where the lower end 51*b* of the dispensing tip 51 is below the liquid surface. This prevents air from being mixed into the liquid during the stirring through aspiration and discharge, and thus, preparation of the emulsion can be appropriately performed.

With reference back to FIG. 18, when the stirring through aspiration and discharge has ended, the controller 310 causes, in step S206, the dispensing tips 51 attached to the eight nozzles 220 to be detached therefrom and discarded into the disposal bag 13*a*, as described with reference to FIG. 9B. In step S207, with respect to all the columns to be processed, the controller 310 determines whether the processes of steps S202 to S206 have ended. For example, in a case where the number of columns to be processed is set to N by the target well setting section 14*c*, the controller 310 determines whether the processes of steps S202 to S206 have ended, starting with the rearmost column, to the Nth column counted from the rearmost column.

In a case where the processes have not ended for all the columns to be processed, the controller 310 increments the value of the process column by 1 in step S208, and then returns the process to step S202. When the processes have ended for all the columns to be processed, the emulsion preparation process ends.

Next, with reference to FIGS. 20 to 22, the first emulsion breaking process will be described.

Figure 20:
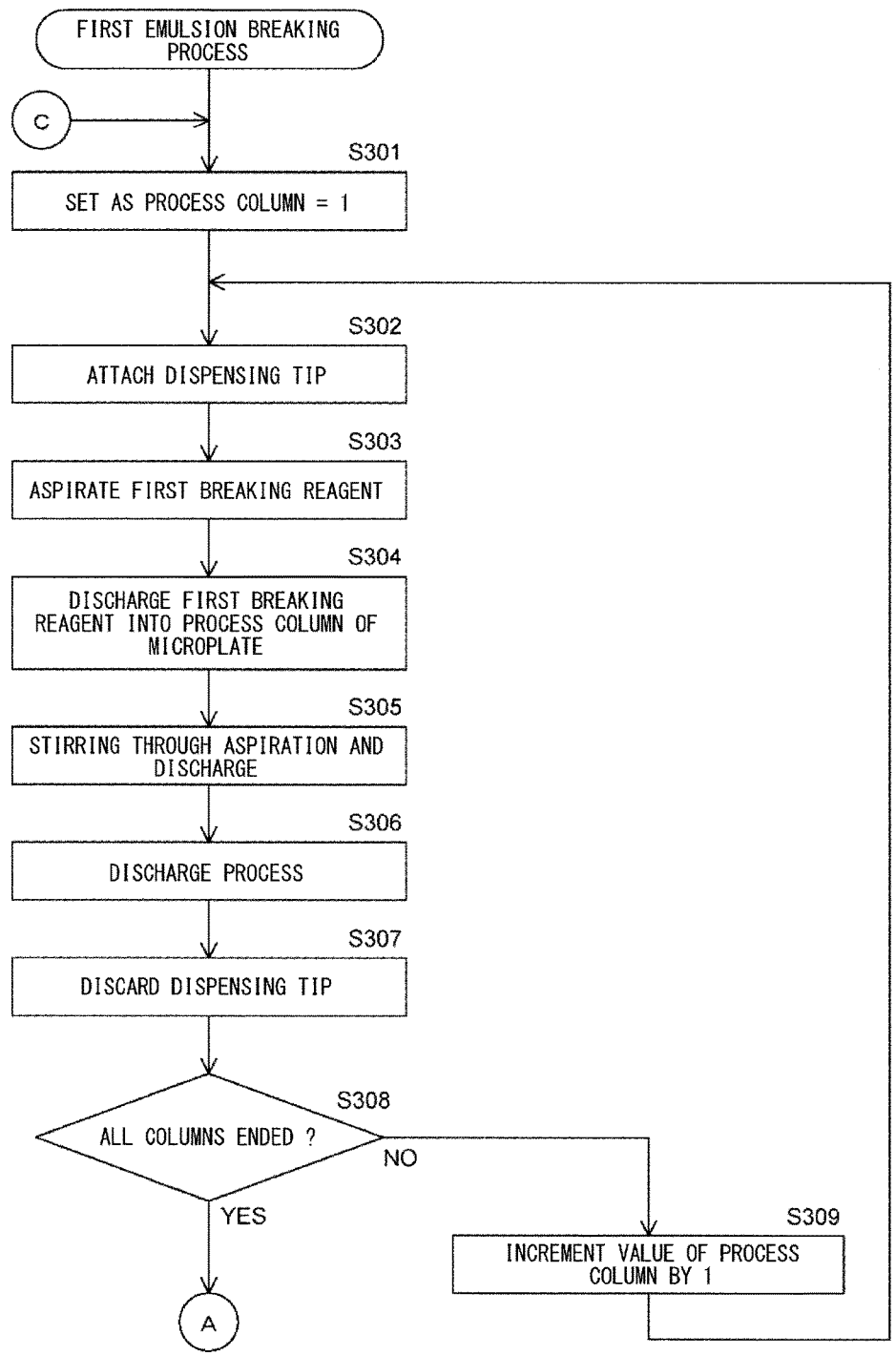
FIG. 20 is a flow chart showing a first emulsion breaking process according to Embodiment 1.

As shown in FIG. 20, in step S301, the controller 310 sets 1 for the process column. In step S302, the controller 310 causes dispensing tips 51 to be attached to the nozzles 220, respectively. In step S303, the controller 310 causes the first breaking reagent in the reagent container 71 placed in the reagent-container placement part 132, to be aspirated. In step S304, the controller 310 causes the first breaking reagent to be discharged into the process column of the microplate 61.

In step S305, the controller 310 causes the liquid in each well 61*a* to be stirred through aspiration and discharge thereof. Here, when step S305 is performed for the first time, the stirring through aspiration and discharge is performed in a state where the lower end 51*b* of the dispensing tip 51 is below the liquid surface, as in step S205 shown in FIG. 18. Accordingly, it is possible to avoid a situation where the emulsion becomes less likely to be broken because the liquid has been clouded with air mixed therein.

When step S305 is performed on the same column for the second time, the stirring through aspiration and discharge is performed such that the lower end 51*b* of the dispensing tip 51 comes above the liquid surface. Specifically, in (d) and (f) of FIG. 19, the discharge is performed in a state where the lower end 51*b* is above the liquid surface. Accordingly, compared with the case where the discharge is performed within the liquid, the stirring can be effectively performed. It should be noted that, when step S305 is performed for the second time, the amount of the oil phase within the liquid has been reduced, and in addition, air is readily released from the liquid due to the alcohol in the liquid. Thus, when step S305 is performed for the second time, even if the discharge is performed from above the liquid surface, air is less likely to be mixed into the liquid.

At the end of the stirring through aspiration and discharge, the controller 310 performs a discharge process in step S306. Specifically, in the last stirring step in the stirring through aspiration and discharge, after the discharge of the liquid has been performed as shown in (g) of FIG. 19, the controller 310 causes the dispensing tip 51 to be raised, thereby spacing the lower end 51*b* of the dispensing tip 51 from the liquid surface in the well 61*a*, and waits for a predetermined time period in the state shown in (h) of FIG. 19. The predetermined time period in this case is a time period necessary for the liquid remaining in the dispensing tip 51 to gather to the lower end 51*b* of the dispensing tip 51, and is set to five seconds, for example. Then, the controller 310 causes the liquid remaining in the dispensing tip 51 to be discharged, and causes the dispensing tip 51 to be raised.

Through this discharge process, substantially all the liquid in the dispensing tip 51 can be discharged into the well 61*a*. Thus, even if the dispensing tip 51 is moved in a horizontal plane after the stirring through aspiration, it is possible to prevent the liquid remaining in the dispensing tip 51 from unintendedly dropping into the apparatus. The discharge after the waiting for the predetermined time period may be repeated a plurality of times. That is, a process may be performed in which: discharge is performed after the waiting for the predetermined time period, and then again, a small amount of air is aspirated into the dispensing tip 51 and then this air is discharged from the dispensing tip 51. Accordingly, the liquid remaining in the dispensing tip 51 can be more completely discharged into the well 61*a*.

The discharge process is not limited to the above procedure, and may be performed in the following manner, for example. In the last stirring step of the stirring through aspiration and discharge, the controller 310 causes the liquid in the dispensing tip 51 to be discharged to an extent that a small amount of the liquid remains in the dispensing tip 51; causes the dispensing tip 51 to be located at a position where only the lower end 51*b* of the dispensing tip 51 is present in the liquid in the well 61*a*; and then, waits for a predetermined time period. Then, while causing the liquid remaining in the dispensing tip 51 to be discharged, the controller 310 causes the dispensing tip 51 to be raised, thereby spacing the lower end 51*b* of the dispensing tip 51 from the liquid surface of the well 61*a*. Also in this case, substantially all the liquid in the dispensing tip 51 can be discharged into the well 61*a*. According to this procedure, in a case where the liquid has a high viscosity, an effect can be obtained that the liquid remaining in the dispensing tip 51 is pulled and extracted by the liquid in the well 61*a*.

In step S307, the controller 310 causes the dispensing tips 51 attached to the nozzles 220 to be discarded. In step S308, with respect to all the columns to be processed, the controller 310 determines whether the processes of steps S302 to S307 have ended. When the processes have not ended for all the columns to be processed, the controller 310 increments the value of the process column by 1 in step S309, and then returns the process to step S302. When the processes have ended for all the columns to be processed, the process is advanced to step S310 in FIG. 21.

Figure 21:
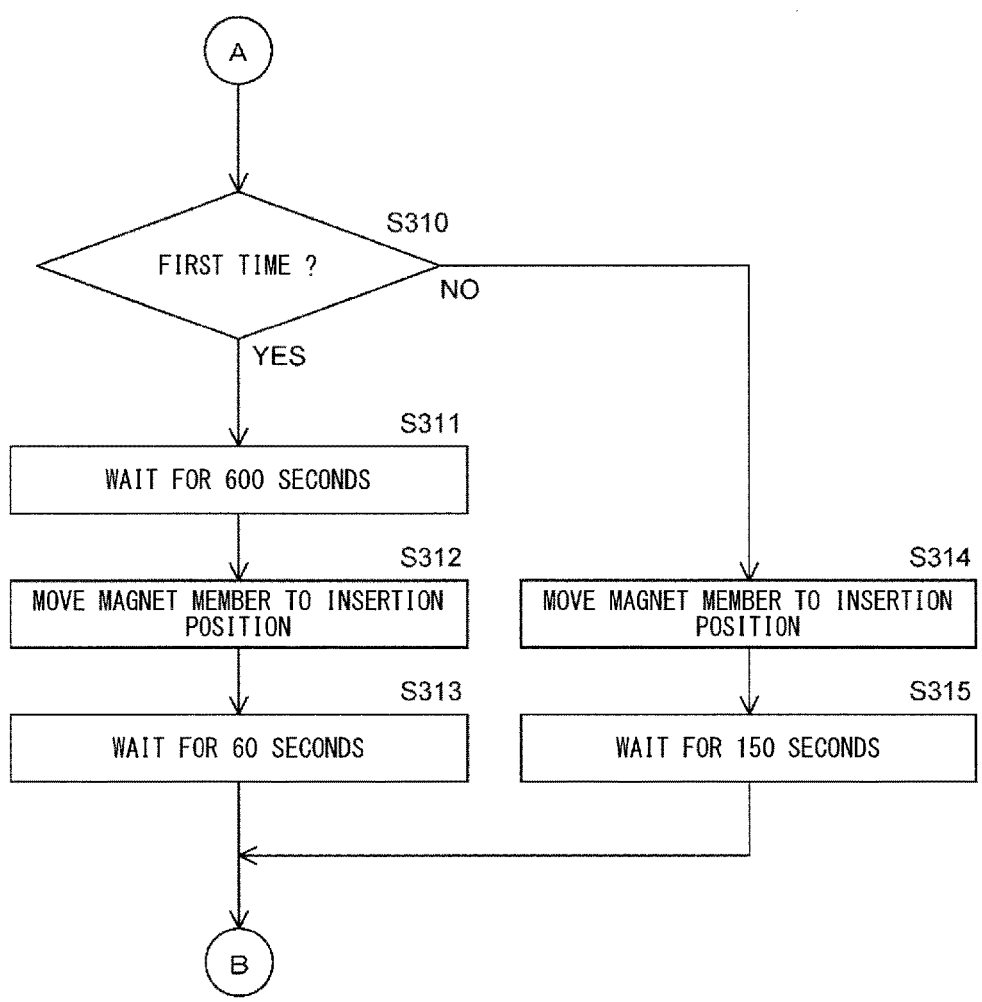
FIG. 21 is a flow chart showing the first emulsion breaking process according to Embodiment 1.

As shown in FIG. 21, in step S310, the controller 310 determines whether the breaking process is the one performed for the first time. The breaking process in step S310 is the processes from step S301 in FIG. 20 to step S323 in FIG. 22. The breaking process is repeated twice in the first emulsion breaking process as described later.

In a case where the breaking process is the one performed for the first time, the controller 310 waits for a predetermined time period in step S311. The predetermined time period in this case is a time period necessary for stabilizing the state of the liquid in the well 61*a*, and is set to 600 seconds, for example. As a result, the emulsion in the well 61a is broken, and the aqueous phase and the oil phase are separated from each other in the well 61a. In addition, thanks to this waiting in step S311, variation among columns in the advancement degrees of the breaking of the emulsion and the separation of the liquid is suppressed.

When the waiting time period in step S311 has elapsed, the controller 310 causes the magnet members 80 to be moved to the insertion position 81 in step S312. Accordingly, the magnetic attraction process by the magnet members 80 is started. Upon the start of the magnetic attraction process, magnetic beads in each well 61a are attracted to the lateral surface of the well 61a. In step S313, the controller 310 waits for 60 seconds. How much waiting time is to be provided immediately after the start of the magnetic attraction process is determined depending on the state and the like of the liquid in the well 61a. If a waiting time period is provided immediately after the start of the magnetic attraction process, attraction of magnetic beads in the well 61a can be stabilized.

On the other hand, in a case where the breaking process is the one performed for the second time, the controller 310 causes the magnet members 80 to be moved to the insertion position 81 in step S314. In the case where the breaking process is the one performed for the second time, the breaking of the emulsion has already been advanced, which is different from the case where the breaking process is the one performed for the first time. Thus, the process can be immediately advanced to the magnetic attraction process. Therefore, in the case where the breaking process is the one performed for the second time, after the first breaking reagent has been dispensed, the process is shifted to the magnetic attraction process, without waiting for a predetermined time period. Accordingly, the time period needed for the emulsion preparation process can be shortened. In step S315, the controller 310 waits for 150 seconds. When the waiting time period in step S313, S315 has elapsed, the process is advanced to step S316 in FIG. 22.

The reason why the waiting time period in step S315 is set to be longer than the waiting time period in step S313 is as follows. In the breaking process for the first time, the oil phase and the aqueous phase separate from each other in the up and down directions in the well 61a, while 600 seconds elapse in step S311. At this time, since most of the magnetic beads are contained in the aqueous phase which is on the lower side, it can be considered that those magnetic beads are present close to the magnet members 80 during the magnetic attraction process in step S312. Thus, the waiting for about 60 seconds in step S313 will allow the magnetic beads to be attracted to the lateral surface of the well 61a. In contrast, in the breaking process for the second time, since the oil phase has substantially removed through the breaking process of the first time, it can be considered that the magnetic beads are dispersed in the whole liquid held in the well 61a. Therefore, it takes time to attract the magnetic beads near the liquid surface to the lower lateral surface of the well 61a through the magnetic attraction process. Thus, in the breaking process for the second time, in step S315, a waiting time period longer than that in step S313 is set. Accordingly, in the breaking process for the second time, the magnetic beads can be more reliably attracted to the lower lateral surface of the well 61a.

Figure 22:
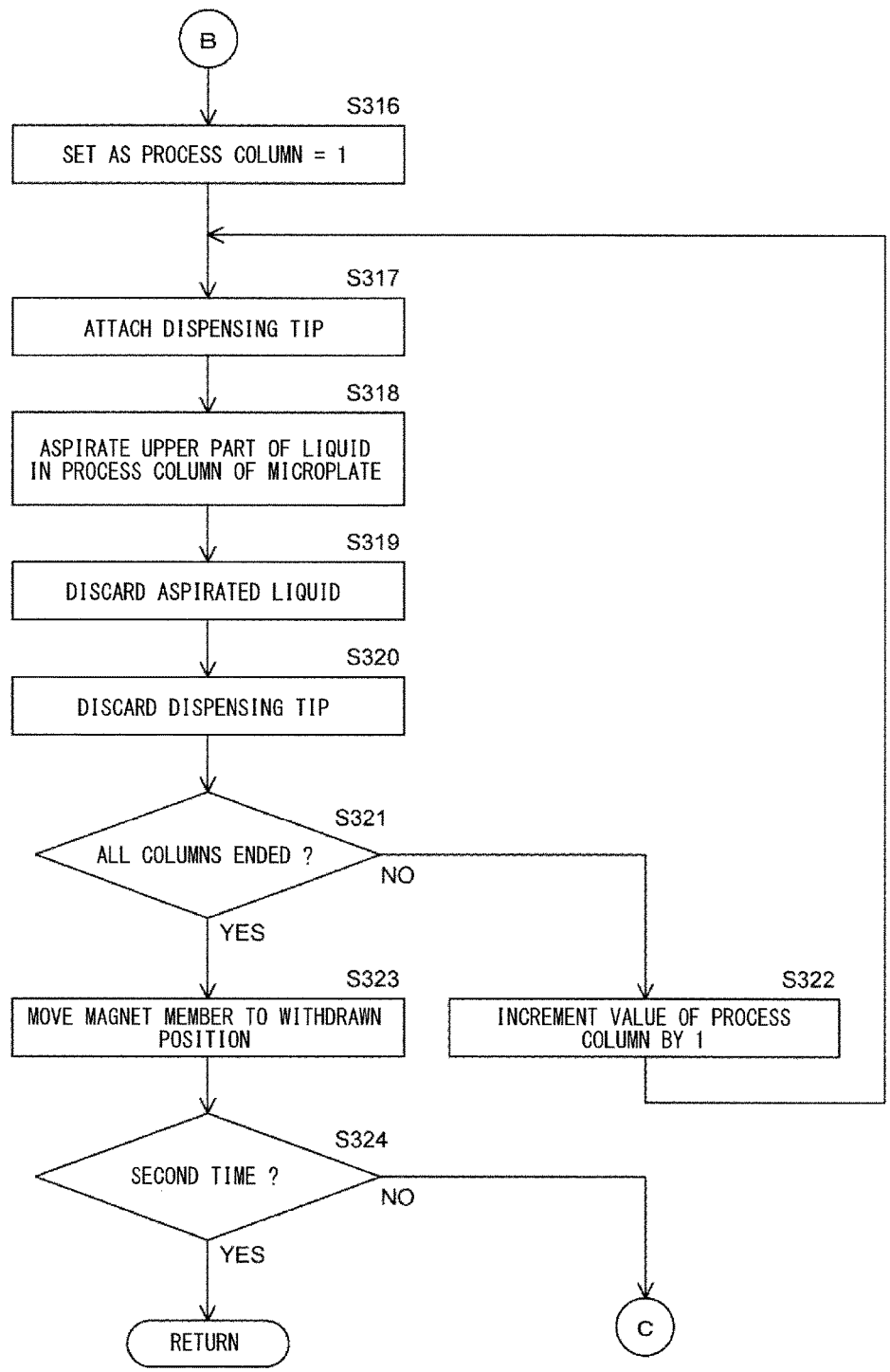
FIG. 22 is a flow chart showing the first emulsion breaking process according to Embodiment 1.

As shown in FIG. 22, in step S316, the controller 310 sets 1 for the process column. In step S317, the controller 310 causes dispensing tips 51 to be attached to the nozzles 220. In step S318, the controller 310 causes the upper part of the liquid in each well 61a in the process column of the microplate 61, to be aspirated. Through the process of step S318, the oil phase, which is on the upper side, excluding the aqueous phase is removed from the well 61a in a state where the magnetic beads remain in the well 61a. In step S319, the controller 310 causes the dispensing tips 51 to be moved to the reagent container 71 for waste liquid which has been placed in the reagent-container placement part 131, and then the controller 310 causes the aspirated liquid to be discharged and discarded into the reagent container 71. In step S320, the controller 310 causes the dispensing tips 51 attached to the nozzles 220, to be discarded.

In the breaking process for the first time, as described above, after the lapse of waiting time for 600 seconds in step S311 shown in FIG. 21, the liquid in the well 61a separates in the up-down direction into the oil phase and the aqueous phase. Thus, in the breaking process for the first time, most of the oil phase is aspirated in step S318, and then discarded in step S319.

In step S321, with respect to all the columns to be processed, the controller 310 determines whether the processes of steps S317 to S320 have ended. When the processes have not ended for all the columns to be processed, the controller 310 increments the value of the process column by 1 in step S322, and then returns the process to step S317. When the processes have ended for all the columns to be processed, the controller 310 causes the magnet members 80 to be moved to the withdrawn position 82 in step S323. Accordingly, the magnetic attraction process performed by the magnet members 80 ends.

In step S324, the controller 310 determines whether the breaking process for the second time has ended, i.e., whether the processes of step S301 in FIG. 20 to step S323 in FIG. 22 have been repeated twice. When the breaking process for the second time has not ended, the process is returned to step S301 in FIG. 20, and then, the breaking process for the second time is started. When the breaking process for the second time has ended, the first emulsion breaking process ends. The breaking process may be performed three times or more, instead of twice.

Next, with reference to FIGS. 23 to 25, the second emulsion breaking process will be described.

Figure 23:
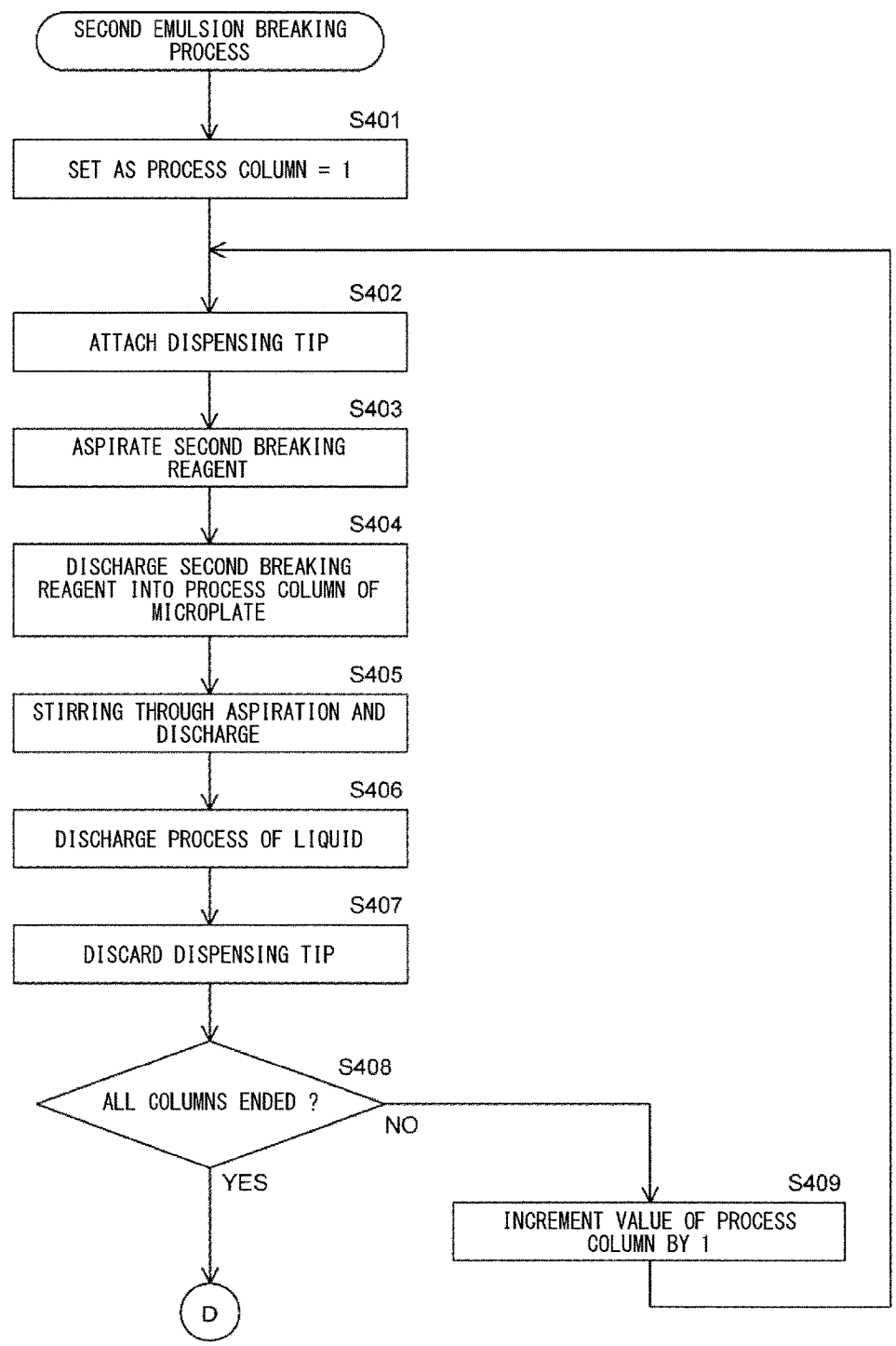
FIG. 23 is a flow chart showing a second emulsion breaking process according to Embodiment 1.

As shown in FIG. 23, in step S401, the controller 310 sets 1 for the process column. In step S402, the controller 310 causes dispensing tips 51 to be attached to the nozzles 220. In step S403, the controller 310 causes the second breaking reagent in the reagent container 71 placed in the reagent-container placement part 133, to be aspirated. In step S404, the controller 310 causes the second breaking reagent to be discharged into the process column of the microplate 61. In step S405, the controller 310 causes the liquid in each well 61a to be stirred through aspiration and discharge thereof.

The stirring through aspiration and discharge in step S405 is performed such that the lower end 51b of the dispensing tip 51 comes above the liquid surface, as in the second execution of step S305 in FIG. 20. Also in this case, for the same reason as in the second execution of step S305, the discharge can be performed from above the liquid surface. Even if air is mixed into the liquid in the stirring process in step S405, the liquid is heated by the thermal cycler in the hybridization process which is performed thereafter. Thus, since the air mixed in the liquid can be removed accordingly, the hybridization process can be appropriately performed.

At the end of the stirring through aspiration and discharge, the controller 310 performs the above-described discharge process in step S406. In step S407, the controller 310 causes the dispensing tips 51 attached to the nozzle 220 to be discarded. In step S408, with respect to all the columns to be processed, the controller 310 determines whether the processes of steps S402 to S407 have ended. When the processes have not ended for all the columns to be processed, the controller 310 increments the value of the process column by 1 in step S409 and then returns the process to step S402. When the processes have ended for all the columns to be processed, the process is advanced to step S410 in FIG. 24.

Figure 24:
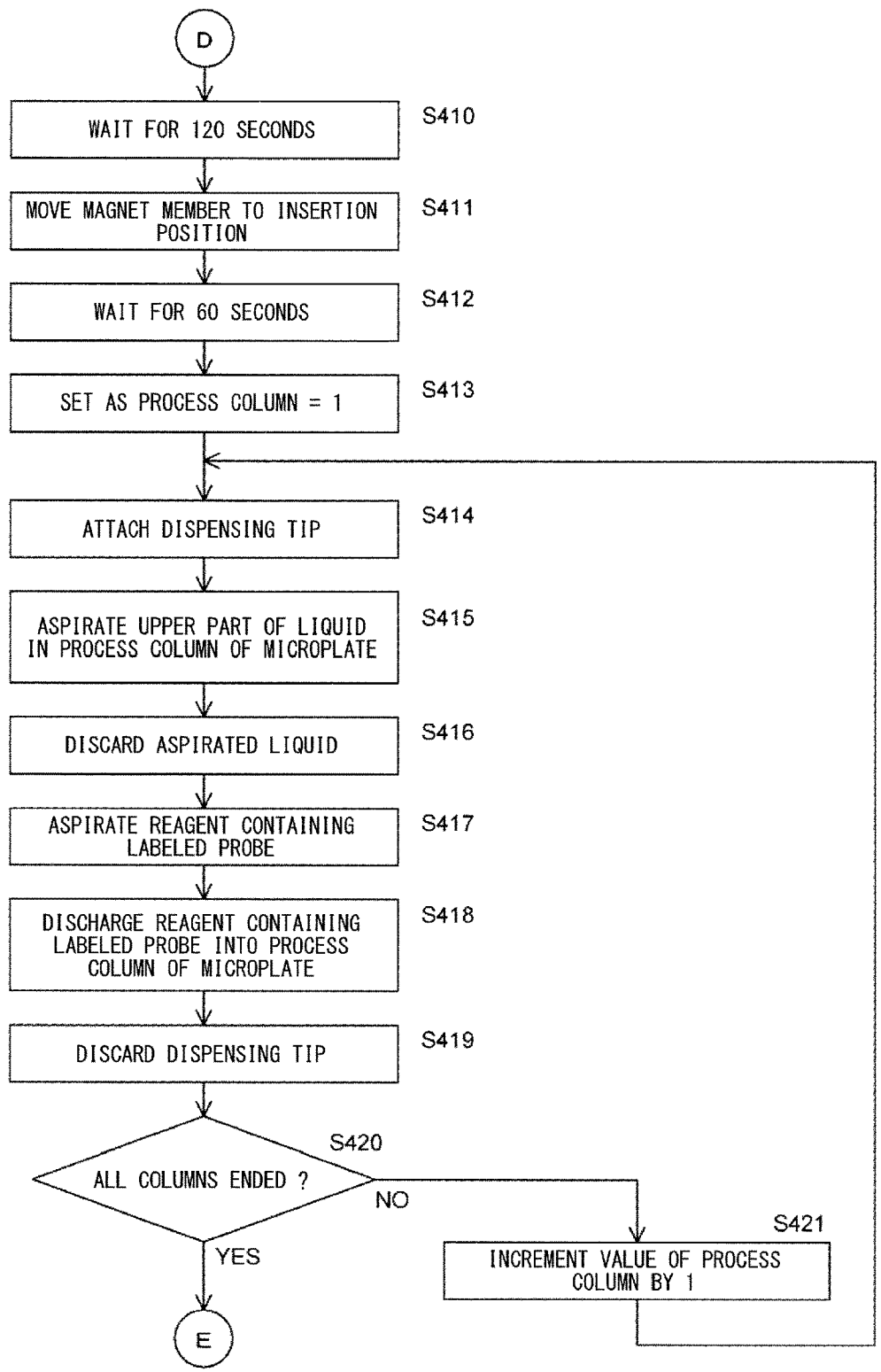
FIG. 24 is a flow chart showing the second emulsion breaking process according to Embodiment 1.

As shown in FIG. 24, in step S410, the controller 310 waits for a predetermined time period. The predetermined time period in this case is a time period necessary for stabilizing the state of the liquid in the well 61a, and is set to 120 seconds, for example. Accordingly, the state of the target DNA molecules in the well 61a is stabilized. When the predetermined time period in step S410 has elapsed, the controller 310 causes the magnet members 80 to be moved to the insertion position 81 in step S411, and then waits for 60 seconds in step S412.

In step S413, the controller 310 sets 1 for the process column. In step S414, the controller 310 causes dispensing tips 51 to be attached to the nozzles 220. In step S415, the controller 310 causes the upper part of the liquid in each well 61a in the process column of the microplate 61, to be aspirated. Also in this case, the oil phase, which is on the upper side, excluding the aqueous phase is removed from the well 61a in a state where the magnetic beads remain in the well 61a. In step S416, the controller 310 causes the aspirated liquid to be discharged and discarded into the reagent container 71 placed in the reagent-container placement part 131.

Subsequently, in step S417, among the columns of the reagent holding portions 62a in the reagent container 62 placed in the reagent-container placement part 141, from the reagent holding portions 62a in the same column as the process column of the microplate 61, the controller 310 causes the reagent containing the labeled probes, to be aspirated. In step S418, the controller 310 causes the reagent containing the labeled probes to be discharged into the process column of the microplate 61. In step S419, the controller 310 causes the dispensing tips 51 attached to the nozzles 220, to be discarded.

In this manner, without new dispensing tips 51 being attached again after the aspiration and discard of the unnecessary liquid performed in step S415 and S416, the dispensing tips 51 that have been used in the discard of the liquid are used to aspirate the reagent containing the labeled probes. Then, the aspirated reagent containing the labeled probes is discharged into each well 61a having magnetic beads remaining therein.

Here, from the viewpoint of preventing contamination at the time of aspiration of a reagent, it can be assumed that new dispensing tips 51 are attached again when the reagent in the reagent container 62 is to be aspirated. However, in Embodiment 1, the reagent in a reagent holding portion 62a of the reagent container 62 from which aspiration has been performed once will not be aspirated thereafter. That is, each reagent holding portion 62a of the reagent container 62 is configured to hold a reagent only by an amount that is needed for one process. Therefore, in Embodiment 1, the dispensing tips 51 that have been used for discarding the liquid can be used to aspirate the reagent containing the labeled probes. Accordingly, compared with a case where new dispensing tips 51 are attached again, the consumption amount of dispensing tips 51 can be suppressed, and thus, burden to environments can be reduced. Moreover, even in a case where the magnetic beads attracted to the lateral surface of the well 61a are in contact with air after the liquid in the well 61a has been aspirated in step S415, the reagent containing the labeled probes is immediately discharged into the well 61a. Thus, the magnetic beads attracted to the lateral surface of the well 61a can be suppressed from being dried and aggregated.

In step S420, with respect to all the columns to be processed, the controller 310 determines whether the processes of steps S414 to S419 have ended. When the processes have not ended for all the columns to be processed, the controller 310 increments the value of the process column by 1 in step S421, and then returns the process to step S414. When the processes have ended for all the columns to be processed, the process is advanced to step S422 in FIG. 25.

Figure 25:
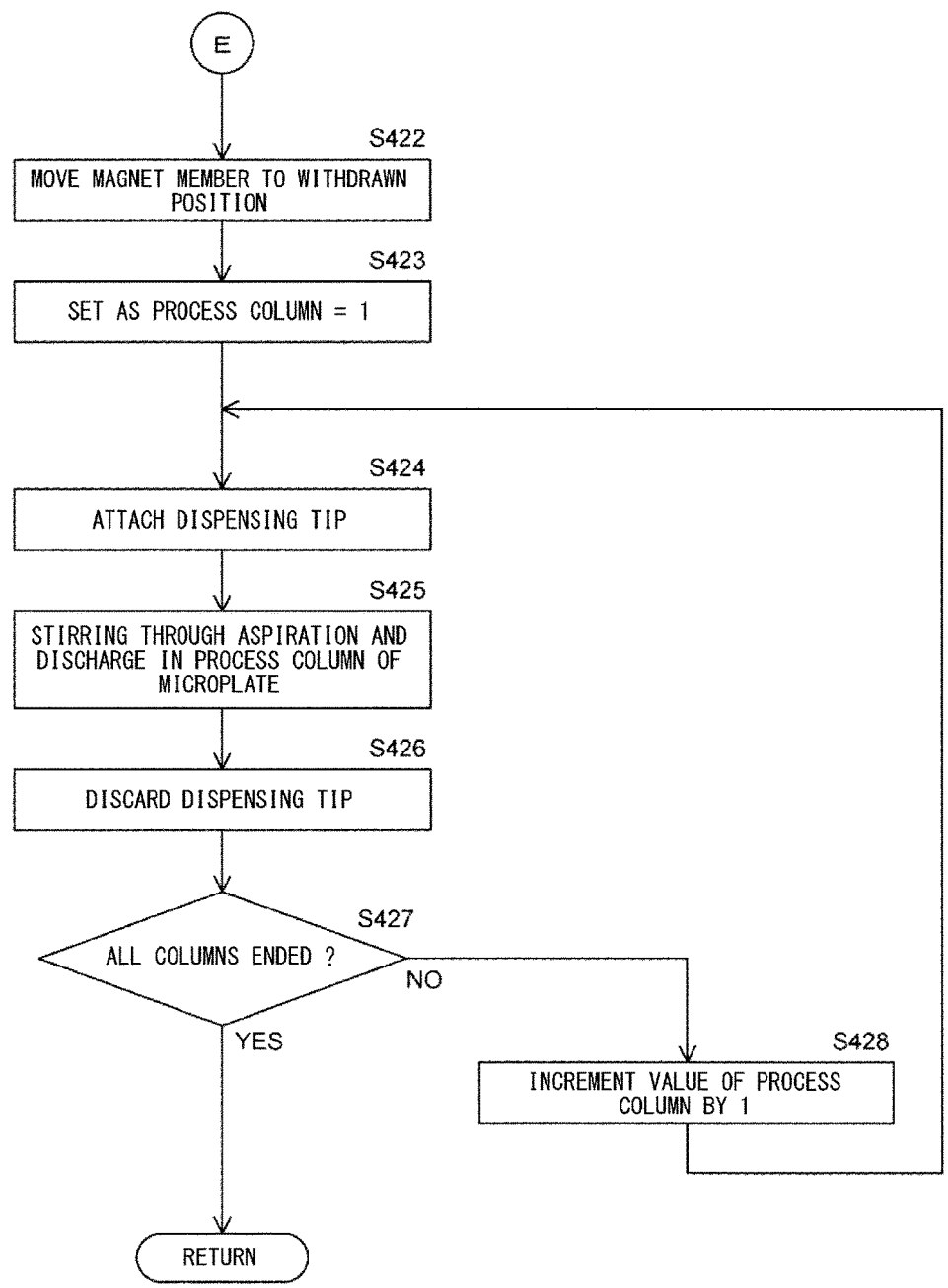
FIG. 25 is a flow chart showing the second emulsion breaking process according to Embodiment 1.

As shown in FIG. 25, in step S422, the controller 310 causes the magnet members 80 to be moved to the withdrawn position 82. In step S423, the controller 310 sets 1 for the process column.

In step S424, the controller 310 causes dispensing tips 51 to be attached to the nozzles 220. In step S425, the controller 310 causes the liquid in each well 61a in the process column of the microplate 61, to be stirred through aspiration and discharge thereof in the manner as described above. As in step S405 in FIG. 23, the stirring through aspiration and discharge in step S425 is performed such that the lower end 51b of the dispensing tip 51 comes above the liquid surface. Also in this case, for the same reason in step S405, the discharge can be performed from above the liquid surface.

Through the process of step S425, the well 61a enters a state that allows the hybridization process to be efficiently performed. In step S426, the controller 310 causes the dispensing tips 51 attached to the nozzles 220 to be discarded. In step S427, with respect to all the columns to be processed, the controller 310 determines whether the processes of steps S424 to S426 have ended. When the processes have not ended for all the columns to be processed, the controller 310 increments the value of the process column by 1 in step S428, and then returns the process to step S424. When the processes have ended for all the columns to be processed, the second emulsion breaking process ends.

Next, with reference to FIGS. 26 and 27, the washing process will be described.

Figure 26:
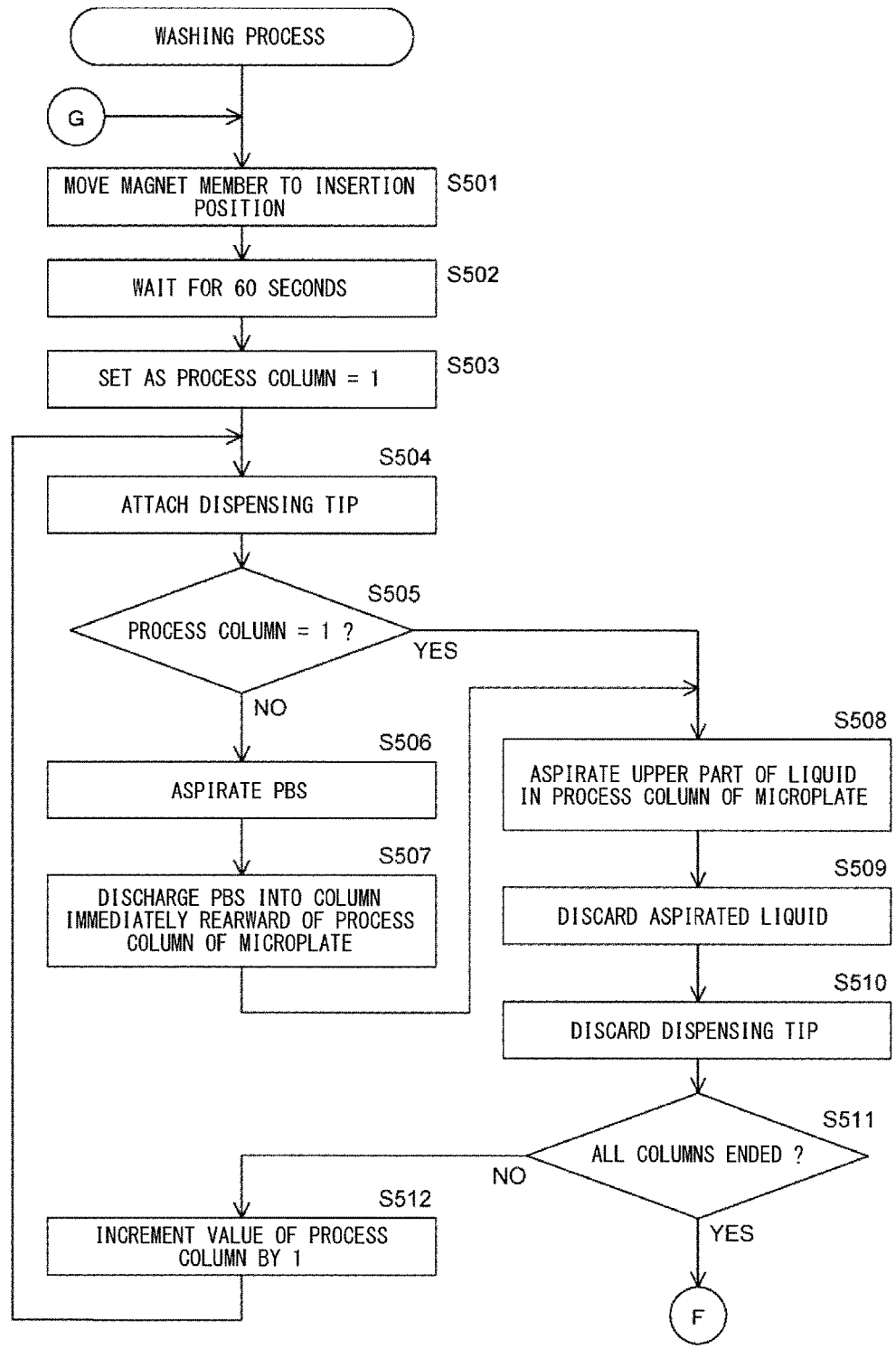
FIG. 26 is a flow chart showing a washing process according to Embodiment 1.

As shown in FIG. 26, the controller 310 causes the magnet members 80 to be moved to the insertion position 81 in step S501, and waits for 60 seconds in step S502. Accordingly, the magnetic beads are attracted. In step S503, the controller 310 sets 1 for the process column. In step S504, the controller 310 causes dispensing tips 51 to be attached to the nozzles 220. In step S505, the controller 310 determines whether the value of the process column is 1, i.e., whether the process column is the rearmost column.

Since the process column has been set to the rearmost column of the microplate 61 when the process had been advanced from step S503 to step S504, it is determined, in step S505, that the process column is the rearmost column. In this case, in step S508, the controller 310 causes the upper part of the liquid in each well 61a in the process column of the microplate 61, to be aspirated. At this time, labeled probes bound to magnetic beads via the target DNA molecules have been attracted by the magnet members 80. Therefore, labeled probes that remain unreacted, i.e., labeled probes that have not been bound to magnetic beads via the target DNA molecules are removed from the well 61a. In step S509, the controller 310 causes the aspirated liquid to be discharged and discarded into the reagent container 71 placed in the reagent-container placement part 131. In step S510, the controller 310 causes the dispensing tips 51 attached to the nozzles 220, to be discarded.

In step S511, with respect to all the columns to be processed, the controller 310 determines whether the processes of steps S504 to S510 have ended. Since the processes have not ended for all the columns to be processed, the controller 310 increments the value of the process column by 1 in step S512, and then returns the process to step S504.

With reference back to step S504, the controller 310 causes dispensing tips 51 to be attached to the nozzles 220, and determines whether the process column is the rearmost column in step S505. Since the current process column is the column immediately forward of the rearmost column, the controller 310 determines that the process column is a column other than the rearmost column, and causes the PBS in the reagent container 71 placed in the reagent-container placement part 132, to be aspirated in step S506. In step S507, the controller 310 causes the PBS to be discharged into the column immediately rearward of the current process column of the microplate 61, i.e., the rearmost column. Accordingly, the PBS is supplied immediately after the liquid has been discarded from each well 61a of the rearmost column. Thus, the inside of the well 61a can be prevented from being dried and the magnetic beads in the well 61a can be suppressed from being aggregated. Once the magnetic beads have been aggregated, even if the PBS is supplied thereafter, the PBS becomes less likely to penetrate into the aggregation of the magnetic beads, and thus, the magnetic beads become less likely to be dispersed. This prevents accurate measurement by the flow cytometer from being performed. Thanks to the process of step S507, the inside of the well 61a can be prevented from being dried after the liquid has been discarded, and the magnetic beads can be appropriately dispersed when the PBS is supplied. Thus, measurement by the flow cytometer can be accurately performed.

Subsequently, the controller 310 causes the upper part of the liquid in each well 61a in the process column to be aspirated in step S508 by the dispensing tips 51 that have been used in the aspiration of the PBS, without causing those dispensing tips 51 to be replaced with new dispensing tips 51. This allows one dispensing tip 51 to be used both for aspiration of the PBS and for aspiration of the liquid in the well 61a. Thus, the consumption amount of dispensing tips 51 can be reduced. Then, the controller 310 continues the processes of step S509 and thereafter. Then, in step S511, with respect to all the columns to be processed, the controller 310 determines whether the processes of steps S504 to S510 have ended. When the processes have ended for all the columns to be processed, the process is advanced to step S513 in FIG. 27.

Here, among the columns to be processed, with respect to the most front column, the PBS is not yet supplied to the wells 61a therein; and with respect to the columns excluding the most front column, after the upper part of the liquid has been discarded in step S508 and before the upper part of the liquid is discarded from another column, the PBS had been supplied in step S507. With respect to the most front column, the PBS is supplied in step S518 in FIG. 27 described later.

Figure 27:
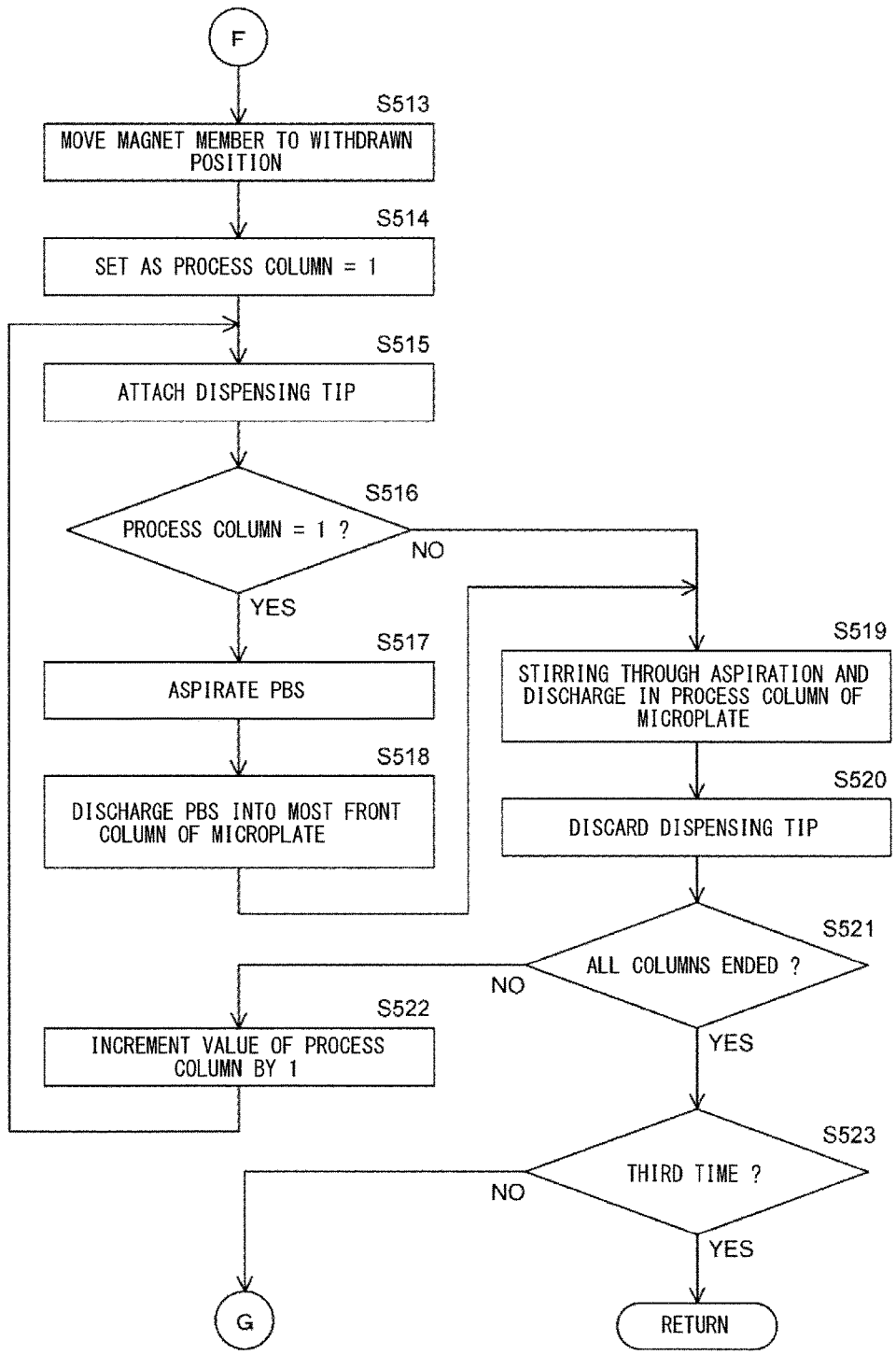
FIG. 27 is a flow chart showing the washing process according to Embodiment 1.

As shown in FIG. 27, in step S513, the controller 310 causes the magnet members 80 to be moved to the withdrawn position 82. In step S514, the controller 310 sets 1 for the process column.

In step S515, the controller 310 causes dispensing tips 51 to be attached to the nozzles 220. In step S516, the controller 310 determines whether the value of the process column is 1, i.e., whether the process column is the rearmost column. When the process column is the rearmost column, the controller 310 causes the PBS in the reagent container 71 placed in the reagent-container placement part 132, to be aspirated in step S517. In step S518, the controller 310 causes the PBS to be discharged into the most front column among the columns to be processed in the microplate 61. On the other hand, when the process column is a column other than the rearmost column, the processes of steps S517 and S518 are skipped.

In step S519, the controller 310 causes the liquid in each well 61a in the process column of the microplate 61, to be stirred through aspiration and discharge thereof in the manner as described above. The stirring through aspiration and discharge in step S519 is performed in a state where the lower end 51b of the dispensing tip 51 is below the liquid surface, as in step S205 in FIG. 18. Accordingly, it is possible to avoid a situation where fluorescence generated from the labeled probes cannot be appropriately detected in the measurement process because air is mixed into the liquid. In step S520, the controller 310 causes the dispensing tips 51 attached to the nozzles 220, to be discarded.

In step S521, with respect to all the columns to be processed, the controller 310 determines whether the processes of steps S515 to S520 have ended. When the processes have not ended for all the columns to be processed, the controller 310 increments the value of the process column by 1 in step S521, and returns the process to step S515. When the processes have ended for all the columns to be processed, the process is advanced to step S523.

In step S523, the controller 310 determines whether processes of step S501 in FIG. 26 to step S522 in FIG. 27 have been performed three times. When the processes have not been performed three times, the process is returned to step S501 in FIG. 26. When the processes have been performed three times, the washing process ends.

Embodiment 2

In Embodiment 2, the specimen processing apparatus 10 performs the PCR process in droplets, the hybridization process, and the measurement process, which are performed in external apparatuses in Embodiment 1. The specimen processing apparatus 10 according to Embodiment 2 is configured to be able to further select a PCR mode, a hybridization mode, or a measurement mode, as the operation mode. It should be noted that the emulsion preparation process and the PCR process may be continuously performed in one operation mode, the emulsion breaking process and the hybridization process may be continuously performed in one operation mode, and the washing process and the measurement process may be continuously performed in one operation mode.

Figure 28A:
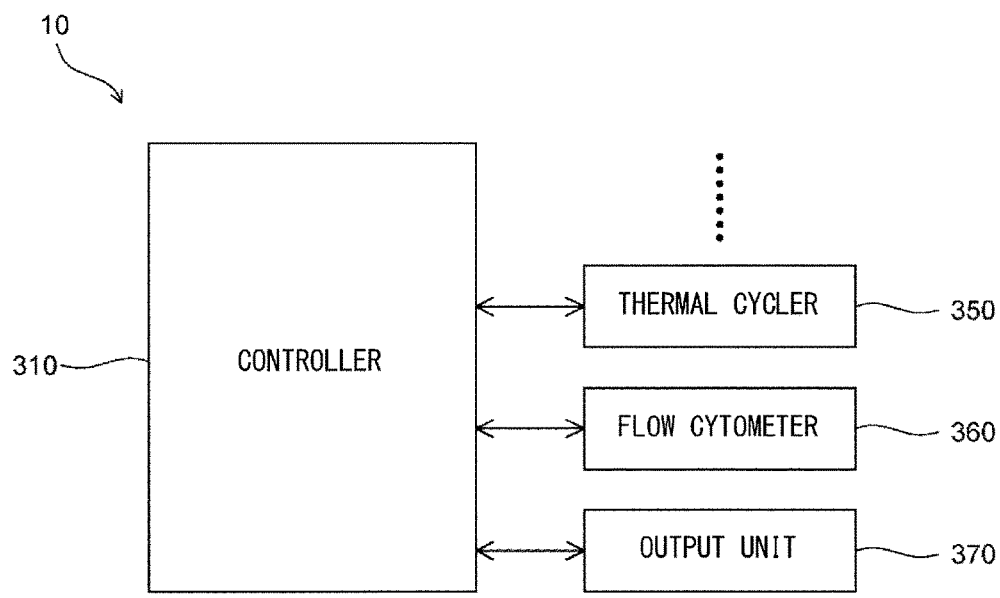
FIG. 28A is a block diagram showing a configuration of a specimen processing apparatus for genetic testing according to Embodiment 2.

As shown in FIG. 28A, the specimen processing apparatus 10 includes a thermal cycler 350, eight flow cytometers 360, and an output unit 370, in addition to the components according to Embodiment 1. The thermal cycler 350, the flow cytometers 360, and the output unit 370 are controlled by the controller 310.

Figure 28B:
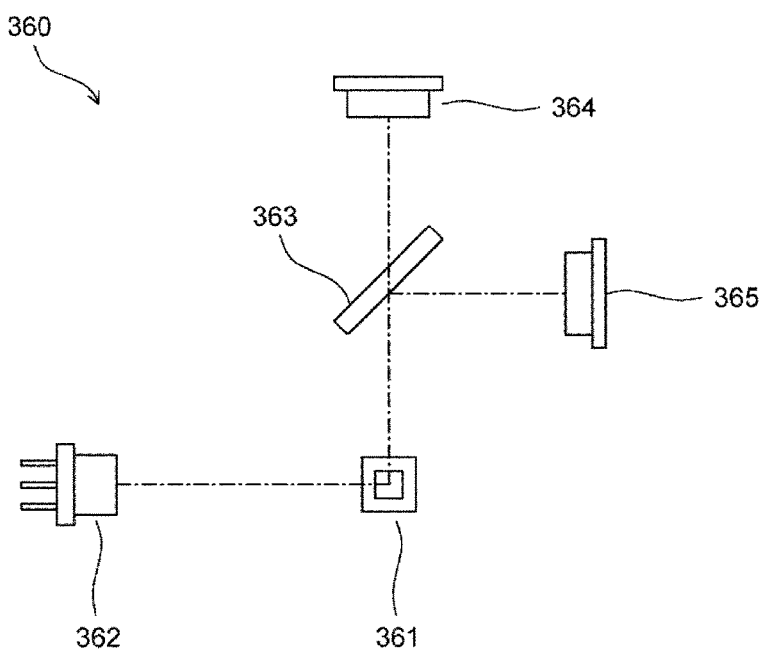
FIG. 28B is a schematic diagram showing a configuration of a flow cytometer.

The thermal cycler 350 includes a heater and a Peltier device. The heater and the Peltier device are configured to be movable immediately above the microplate placement part 121. It may be configured such that the microplate 61 placed in the microplate placement part 121 is gripped by a hand to be transferred to the position of the Peltier device and the heater fixed in the housing 11. As shown in FIG. 28B, each flow cytometer 360 includes a flow cell 361, a laser light source 362, a dichroic mirror 363, and light detectors 364 and 365. The light detectors 364 and 365 are each an avalanche photodiode. The output unit 370 is implemented by a display unit or a communication device.

When the PCR process in droplets is started, the controller 310 drives the thermal cycler 350 so as to perform a process of repeating, a plurality of times, one cycle in which the temperature of the microplate 61 is changed to a plurality of different temperatures. As a result, in each droplet of the W/O type emulsion prepared in the emulsion preparation process, the target DNA molecule is amplified. When the hybridization process is started, the controller 310 drives the thermal cycler 350 so as to perform the process of changing the temperature of the microplate 61 to a plurality of different temperatures. As a result, labeled probes are bound to the target DNA molecules.

When the measurement process is started, the controller 310 drives each flow cytometer 360 so as to measure magnetic beads washed in the washing process, and count magnetic beads to which labeled probes are bound, on the basis of the result of the measurement.

Specifically, the controller 310 causes new dispensing tips 51 to be attached to the nozzles 220, and causes the liquid in the eight wells 61a arranged in the X-axis direction, to be aspirated. The controller 310 causes the liquid aspirated from the eight wells 61a, to be discharged into eight receptacles, respectively. The controller 310 causes the liquid discharged in the eight receptacles, to be sent to the eight flow cytometers 360 connected to the receptacles, respectively. It should be noted that, in a case where the washing process and the measurement process are continuously performed, since the liquid is moved from the wells 61a to the receptacles, the number of dispensing tip containers 50 that are necessary is increased by one compared with that in a case where the washing process is singularly performed.

The specimen processing apparatus 10 may include a single flow cytometer 360. In this case, an aspiration unit for aspirating the liquid from one well 61a of the microplate 61 is separately provided, and by this aspiration unit, the liquid in one well 61a is sent to the single flow cytometer 360.

The liquid, i.e., a measurement sample, sent to the flow cytometer 360 is caused to flow in the flow cell 361. The controller 310 causes the measurement sample flowing in the flow cell 361 to be irradiated with laser light from the laser light source 362. Of the two kinds of fluorescence generated in this manner and having different wavelengths, one kind of fluorescence passes through the dichroic mirror 363 to be applied to the light detector 364, and the other kind of fluorescence is reflected by the dichroic mirror 363 to be applied to the light detector 365.

On the basis of output signals from the light detectors 364 and 365, the controller 310 counts the number of magnetic beads to which the variant DNA molecules in the measurement sample are bound, and the number of magnetic beads to which the wild-type DNA molecules in the measurement sample are bound. The controller 310 obtains the ratio of the number of magnetic beads to which the variant DNA molecules are bound, relative to the total of the number of magnetic beads to which the variant DNA molecules are bound and the number of magnetic beads to which the wild-type DNA molecules are bound. In this manner, for each well 61a, the controller 310 obtains the counted numbers and the ratio, and outputs the obtained counted numbers and ratio to the output unit 370. When the output unit 370 is implemented by a display unit, the obtained counted numbers and ratio are displayed on the output unit 370. When the output unit 370 is implemented by a communication device, the obtained counted number and ratio are outputted to the output unit 370, thereby being sent to another apparatus.

In Embodiment 2, the operator sets the operation mode to any one of the PCR mode, the hybridization mode, and the measurement mode, and then presses the start instruction section 14f, thereby being able to start the corresponding one of the PCR process in droplets, the hybridization process, and the measurement mode. Since all the processes shown in FIG. 13 are automatically performed through simple operations made onto the apparatus, the burden on the laboratory technician can be reduced, and the genetic testing which uses the emulsion can be made efficient.

In the above embodiments, the specimen pretreatment for genetic testing which uses the BEAMing method has been described as an example. However, without being limited thereto, the embodiments can be applied to any specimen pretreatment for genetic testing which uses an emulsion. For example, the embodiments may be applied to a case where: an emulsion having a plurality of droplets dispersed therein is prepared, each droplet containing blood and a latex bead to which a reagent component for amplifying a target nucleic acid molecule in the blood is bound; the target nucleic acid molecule is amplified in each droplet; the emulsion is broken; and the amplified target nucleic acid molecules are collected. As the latex beads, polystyrene beads may be used.

As a method for measuring beads collected from droplets, instead of the method using the flow cytometer, for example, a method may be employed in which: a liquid that contains beads collected from droplets is discharged onto a slide glass; an image of beads on the slide glass is taken; and beads to which labeled probes are bound are counted through image analysis.

What is claimed is:

1. A specimen processing apparatus for genetic testing, the specimen processing apparatus comprising:
   a plurality of dispensing-tip-container placement parts, each configured to place a dispensing-tip-container having a plurality of dispensing tips and having a light emitter for providing an indication that urges placing of the dispensing-tip-container by emitting light;
   a plurality of reagent-container placement parts each configured to place a reagent container containing a reagent and having a light emitter for providing an indication that urges placing of the reagent container by emitting light;
   a microplate placement part in which a microplate having a plurality of wells is placed;
   a dispensing unit configured to attach a dispensing tip with a distal end and aspirate or discharge a liquid using the attached dispensing tip;
   a transfer unit configured to move the dispensing unit to at least one of the dispensing-tip-container placement parts, the reagent-container placement parts and the microplate placement part;
   a mode setting button configured to receive a setting of an operation mode selected by an operator from a plurality of predetermined operation modes including an emulsion preparation mode for preparing an emulsion and an emulsion breaking mode for breaking the emulsion;
   a start button configured to receive a start instruction of the operator to start a process according to the operation mode set by the mode setting button; and
   a controller programmed to:
   when the emulsion preparation mode has been set, control the light emitters so as to provide first indications that urge placing of a first reagent container containing an emulsion reagent for preparing the emulsion and one or more dispensing-tip-containers necessary for an emulsion preparation process, and, in accordance with the start instruction received by the start button, control the transfer unit and the dispensing unit so as to dispense the emulsion reagent contained in the first reagent container placed according to the first indications, into a well of the microplate in the microplate placement part; and when the emulsion breaking mode has been set, control the light emitters so as to provide second indications that urge placing of a second reagent container containing a breaking reagent for breaking the emulsion and one or more dispensing-tip-containers necessary for an emulsion breaking process, and, in accordance with the start instruction received by the start button, control the transfer unit and the dispensing unit so as to dispense the breaking reagent contained in the second reagent container placed according to the second indications, into a well of the microplate in the microplate placement part.

2. The specimen processing apparatus for genetic testing of claim 1, wherein the controller is programmed to control the transfer unit and the dispensing unit so as to aspirate a liquid from the well and discard the liquid after a predetermined time period necessary for stabilizing a state of the liquid in the well has elapsed after the breaking reagent had been dispensed into the well of the microplate.

3. The specimen processing apparatus for genetic testing of claim 1, further comprising:
a target well setting button configured to receive a setting of the number of target wells by the operator among the plurality of wells provided in the microplate, wherein the controller is programmed to control the light emitters so as to indicate the one or more dispensing-tip-container placement parts for which placing of the dispensing-tip-container is urged, on the basis of the number of target wells set by the target well setting button.

4. The specimen processing apparatus for genetic testing of claim 1, wherein the controller is programmed to control the dispensing unit such that: after discharging a reagent into a well of the microplate, the dispensing unit repeats, a plurality of times, a step of stirring the liquid in the well by performing aspirating and discharging the liquid in the well; the dispensing tip is raised after the liquid has been discharged in the last stirring step; after a lapse of a predetermined time period necessary for the liquid remaining in the dispensing tip to gather to a tip of the dispensing tip, the liquid remaining in the dispensing tip is discharged; and then the dispensing tip is raised.

5. The specimen processing apparatus for genetic testing of claim 4, wherein the controller is programmed to control the dispensing unit so as to repeat the discharge in the stirring step at two positions between which a center of the well is located, wherein each of the two positions is located near a lateral surface of the well.

6. The specimen processing apparatus for genetic testing of claim 1, wherein the dispensing unit includes a cylindrical nozzle configured to insert into the dispensing tip, and
a lateral surface of an end portion of the nozzle is partially cut out so as to extend to be closer to a central axis of the nozzle toward a tip of the nozzle.

7. The specimen processing apparatus for genetic testing of claim 1, wherein each of the light-emitters of the dispensing-tip-container placement parts is arranged at a position hidden by the dispensing-tip-container when the dispensing-tip-container is placed in the dispensing-tip-container placement part, and
each of the light-emitters of the reagent-container placement parts is arranged at a position hidden by the reagent container when the reagent container is placed in the reagent-container placement part.

8. The specimen processing apparatus for genetic testing of claim 1, wherein the emulsion is a water-in-oil type (W/O type) emulsion having a plurality of droplets dispersed in an oil phase, and each droplet is composed of an aqueous phase containing a specimen which contains DNA and a bead which has a reagent component necessary for amplifying a target DNA molecule,
the emulsion reagent contains a component for forming the oil phase, and
the well of the microplate accommodates the aqueous phase containing the specimen and the bead.

9. The specimen processing apparatus for genetic testing of claim 8, wherein the bead includes latex beads or magnetic beads.

10. The specimen processing apparatus for genetic testing of claim 8, wherein the reagent component necessary for amplifying the target DNA molecule is a plurality of primer molecules which each bind to the target DNA molecule.

11. The specimen processing apparatus for genetic testing of claim 5, wherein the controller is programmed to repeat a plurality of times a breaking process of sequentially performing steps of dispensing the breaking reagent and aspirating and discarding the liquid from the well, wherein in the breaking process for the first time, the breaking process is shifted to the aspirating step after the predetermined time period has elapsed after the breaking reagent had been dispensed, and in the breaking process for the second time and thereafter, the breaking process is shifted to the aspirating step before the predetermined time period has elapsed after the breaking reagent had been dispensed.

12. The specimen processing apparatus for genetic testing of claim 8, wherein the second indications urge placing of a third reagent container containing a labelling reagent including a labeled probe capable of being hybridized to the amplified target DNA molecule, when the emulsion breaking mode has been set, the controller is programmed to:
control the light emitters so as to provide the second indications that urge placing of the second and third reagent containers and the one or more dispensing-tip-containers; and
control, in accordance with the start instruction received by the start button, the transfer unit and the dispensing unit so as to dispense the labelling reagent, into the well of the microplate placed in the microplate placement part, after the breaking reagent has been dispensed.

13. The specimen processing apparatus for genetic testing of claim 12, wherein the controller is programmed to control the transfer unit and the dispensing unit so as to: after dispensing the breaking reagent, aspirate and discard the liquid from the well to cause the beads to remain in the well; then aspirate the labelling reagent by use of the dispensing tip that has been used in the discarding the liquid, without the dispensing unit having a new dispensing tip attached thereto; and then dispense the labelling reagent into the well where the beads remain.

14. The specimen processing apparatus for genetic testing of claim 12, wherein the third reagent container includes a plurality of reagent holding portions respectively associated with the plurality of wells of the microplate, and the controller is programmed to control the transfer unit and the dispensing unit so as to perform the dispensing of the labelling reagent from the reagent holding portion to the corresponding well.

15. The specimen processing apparatus for genetic testing of claim 12, wherein the mode setting button is configured to receive a setting of a wash mode for separating unreacted labeled probe by performing BF separation in the well of the microplate placed in the microplate placement part, and the controller is programmed to, when the wash mode has been set, control the light emitters so as to provide third indications that urge placing of a fourth reagent container containing a washing reagent and one or more dispensing-tip-container necessary for a washing process, and control, in accordance with the start instruction received by the start button, the transfer unit and the dispensing unit so as to perform the BF separation in the well of the microplate to aspirate and separate the unreacted labeled probe from the beads, and then to dispense the washing reagent contained in the fourth reagent container placed according to the third indications, into the well of the microplate.

16. The specimen processing apparatus for genetic testing of claim 15, wherein the controller is programmed to: when the wash mode has been set, control the transfer unit and the dispensing unit such that, after the unreacted labeled probe has been aspirated and separated from the bead in a first well of the microplate, and before the unreacted labeled probe is aspirated and separated from the bead in a second well which is different from the first well of the microplate, the washing reagent is dispensed into the first well.

17. The specimen processing apparatus for genetic testing of claim 8, wherein the microplate has the wells with an interval in a plurality of rows and in a plurality of columns on a top surface, each of the wells having a concave shape, the specimen processing apparatus comprises:
a magnet member capable of being inserted between the wells protruding on a lower side of the microplate placed in the microplate placement part; and
a magnet member moving unit including a drive unit and configured to move the magnet member by the drive unit to an insertion position and a withdrawn position, the insertion position being a position at which the magnet member is inserted between the wells, and the withdrawn position is a position at which the magnet member is withdrawn from between the wells,
the beads are magnetic beads, and
the controller is programmed to: when a component other than the magnet beads in each well of the microplate is to be aspirated in a state where the magnetic beads remain in the well, control the transfer unit, the dispensing unit, and the magnet member moving unit such that the component other than the magnet beads in the well is aspirated in a state where the magnetic beads are attracted by the magnet member located at the insertion position.

18. The specimen processing apparatus for genetic testing of claim 17, wherein the reagent-container placement parts are provided at a position adjacent to the microplate placement part, the magnet member moving unit is configured to move the magnet member from the insertion position to the withdrawn position which is on a lower side of the reagent-container placement parts by moving the magnet member on a horizontal plane.

19. A specimen processing apparatus for genetic testing, the specimen processing apparatus comprising:

a plurality of dispensing-tip-container placement parts each of which is configured to place a dispensing-tip-container having a plurality of dispensing tips and has a light emitter for performing an indication that urges placing of the dispensing-tip-container by emitting light;
a plurality of reagent-container placement parts each of which is configured to place a reagent container containing a reagent and has a light emitter for performing an indication that urges placing of the reagent container by emitting light;
a microplate placement part in which a microplate having a plurality of wells is placed;
a dispensing unit configured to attach a dispensing tip with a distal end and aspirate or discharge a liquid using the attached dispensing tip;
a transfer unit configured to move the dispensing unit to at least one of the dispensing-tip-container placement parts, the reagent-container placement parts and the microplate placement part;
a mode setting button configured to receive a setting of an operation mode selected by an operator from a plurality of predetermined operation modes including an emulsion breaking mode for breaking an emulsion;
a start button configured to receive a start instruction of the operator to start a process according to the operation mode set by the mode setting button; and
a controller programmed to:
when the emulsion breaking mode has been set, control the light emitters so as to provide indications that urge placing of a reagent container containing a breaking reagent for breaking the emulsion and one or more dispensing-tip-containers necessary for an emulsion breaking process; and
control, in accordance with the start instruction received by the start button, the transfer unit and the dispensing unit so as to dispense the breaking reagent contained in the reagent container placed according to the indications, into a well of the microplate placed in the microplate placement part.

20. A specimen processing apparatus for genetic testing, the specimen processing apparatus comprising:

a plurality of dispensing-tip-container placement parts each configured to place a dispensing-tip-container and a plurality of dispensing tips, and having a light emitter for performing an indication that urges placing of the dispensing-tip-container by emitting light;
a plurality of reagent-container placement parts each configured to place a reagent container containing a reagent and having a light emitter for performing an indication that urges placing of the reagent container by emitting light;
a microplate placement part in which a microplate having a plurality of wells is placed;
a dispensing unit configured to attach a dispensing tip with a distal end and aspirate or discharge a liquid using the attached dispensing tip;
a transfer unit configured to move the dispensing unit to at least one of the dispensing-tip-container placement parts, the reagent-container placement parts and the microplate placement part;
a mode setting button configured to receive a setting of an operation mode selected by an operator from a plurality of predetermined operation modes including an emulsion preparation mode for preparing an emulsion;

a start button configured to receive a start instruction of the operator to start a process according to the operation mode set by the mode setting button; and a controller programmed to:

when the emulsion preparation mode has been set, control the light emitters so as to provide indications that urges placing of a reagent container containing an emulsion reagent for forming the emulsion and one or more dispensing-tip-containers necessary for an emulsion preparation process; and control, in accordance with the start instruction received by the start button, the transfer unit and the dispensing unit so as to dispense the emulsion reagent contained in the reagent container placed according to the indications, into a well of the microplate placed in the microplate placement part.

* * * * *